US012637437B2

(12) United States Patent
Burton et al.

(10) Patent No.: US 12,637,437 B2
(45) Date of Patent: May 26, 2026

(54) HERBICIDAL COMPOUNDS

(71) Applicant: SYNGENTA CROP PROTECTION AG, Basel (CH)

(72) Inventors: Paul Matthew Burton, Bracknell (GB); Glynn Mitchell, Bracknell (GB); Nicholas John Taylor, Bracknell (GB); Sarah Armstrong, Bracknell (GB)

(73) Assignee: SYNGENTA CROP PROTECTION AG, Basel (CH)

( * ) Notice: Subject to any disclaimer, the term of this patent is extended or adjusted under 35 U.S.C. 154(b) by 252 days.

(21) Appl. No.: 18/559,458

(22) PCT Filed: Apr. 29, 2022

(86) PCT No.: PCT/EP2022/061494

§ 371 (c)(1),
(2) Date: Nov. 7, 2023

(87) PCT Pub. No.: WO2022/233727

PCT Pub. Date: Nov. 10, 2022

(65) Prior Publication Data

US 2024/0254094 A1 Aug. 1, 2024

(30) Foreign Application Priority Data

May 7, 2021 (GB) ..................................... 2106554

(51) Int. Cl.

| | |
|---|---|
| ***C07D 257/06*** | (2006.01) |
| ***A01N 25/32*** | (2006.01) |
| ***A01N 47/06*** | (2006.01) |
| ***A01N 47/18*** | (2006.01) |
| ***A01P 13/00*** | (2006.01) |
| ***C07D 401/12*** | (2006.01) |
| ***C07D 405/12*** | (2006.01) |
| ***C07D 413/12*** | (2006.01) |

(52) U.S. Cl.

CPC ........... *C07D 257/06* (2013.01); *A01N 25/32* (2013.01); *A01N 47/06* (2013.01); *A01N 47/18* (2013.01); *A01P 13/00* (2021.08); *C07D 401/12* (2013.01); *C07D 405/12* (2013.01); *C07D 413/12* (2013.01)

(58) Field of Classification Search

CPC .. C07D 257/06; C07D 401/12; C07D 405/12; C07D 413/12; A01N 25/32; A01N 47/06; A01N 47/18; A01P 13/00

See application file for complete search history.

(56) References Cited

U.S. PATENT DOCUMENTS

| | | | |
|---|---|---|---|
| 8,481,749 | B2 | 7/2013 | Braun et al. |
| 2012/0058892 | A1 | 3/2012 | Braun et al. |
| 2014/0179527 | A1 | 6/2014 | Braun et al. |

FOREIGN PATENT DOCUMENTS

| | | | |
|---|---|---|---|
| WO | 2012028579 | A1 | 3/2012 |
| WO | 2019141740 | A1 | 7/2019 |
| WO | 2019243358 | A1 | 12/2019 |
| WO | 2021209383 | A1 | 10/2021 |

OTHER PUBLICATIONS

International Search Report and Written Opinion of the International Searching Authority issued in International Patent Application No. PCT/EP2022/061494 dated Jul. 4, 2022.

UKIPO; Search Report under Section 17 issued in GB App. No. 2106554.5, dated Oct. 26, 2021.

*Primary Examiner* — Trevor Love

(74) *Attorney, Agent, or Firm* — BakerHostetler; Toni-Junell Herbert

(57) ABSTRACT

The present invention related to compounds of Formula (I) or an agronomically acceptable salt thereof, wherein $R^1$, $R^2$, $R^3$, $R^4$ and $R^5$ are as described herein. The invention further relates to compositions comprising said compounds, to methods of controlling weeds using said compositions, to the use of Compounds of Formula (I) as a herbicide, and methods of making said compounds.

(I)

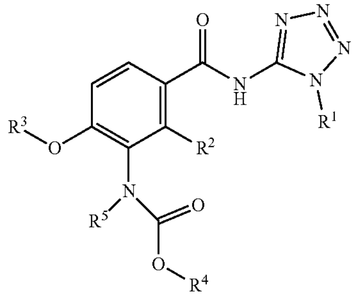

20 Claims, No Drawings

HERBICIDAL COMPOUNDS

CROSS-REFERENCE TO RELATED APPLICATIONS

This application is a U.S. National Stage Application, filed under 35 U.S.C. § 371, of International Application No. PCT/EP2022/061494, filed Apr. 29, 2022, which claims priority to GB 2106554.5, filed May 7, 2021, the entire contents of which are incorporated by reference herein.

The present invention relates to novel herbicidal compounds, to processes for their preparation, to herbicidal compositions which comprise the novel compounds, and to their use for controlling weeds, in particular in crops of useful plants, or for inhibiting plant growth.

N-(tetrazol-5-yl)arylcarboxamides are disclosed in, for example, WO2012/028579. The present invention relates to novel arylcarboxamides.

Thus, according to the present invention there is provided a compound of Formula (I):

(I)

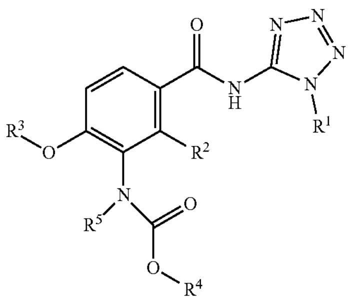

or an agronomically acceptable salt thereof, wherein:—

$R^1$ is selected from the group consisting of $C_1$-$C_4$alkyl-, $C_1$-$C_4$haloalkyl-, $C_1$-$C_4$alkoxy-$C_1$-$C_4$alkyl- and $C_1$-$C_4$haloalkoxy-$C_1$-$C_4$alkyl-;

$R^2$ is selected from the group consisting of halogen, $C_1$-$C_6$alkyl-, $C_1$-$C_3$alkoxy-, $C_1$-$C_6$ haloalkyl- and —$S(O)_pC_1$-$C_6$alkyl;

$R^3$ is $C_1$-$C_6$haloalkyl;

$R^4$ is selected from the group consisting of $C_1$-$C_6$alkyl-, $C_1$-$C_6$haloalkyl-, $C_1$-$C_3$alkoxy-$C_1$-$C_3$alkyl-, $C_1$-$C_4$haloalkoxy-$C_1$-$C_4$alkyl-, $C_1$-$C_4$alkoxy-$C_1$-$C_4$haloalkyl-, $C_1$-$C_3$alkyl-$S(O)_pC_1$-$C_3$alkyl-, cyano-$C_1$-$C_6$alkyl-, —$(CH_2)_n$—$CHR^6R^7$, $C_3$-$C_6$cycloalkyl- and $C_3$-$C_6$cycloalkyl-$C_1$-$C_3$alkyl- wherein either $C_3$-$C_6$cycloalkyl may be optionally substituted by one or two fluorine atoms; and $R^5$ is selected from the group consisting of hydrogen, $C_1$-$C_6$alkyl-, $C_1$-$C_6$haloalkyl and $C_3$-$C_6$cycloalkyl; or $R^4$ and $R^5$ together are —$(CH_2)_m$—, and $R^6$ and $R^7$ together with the carbon atom to which they are attached form a saturated 4-, 5- or 6-membered heterocycle which is optionally substituted; and m is 2 or 3, n is 0, 1, 2 or 3, and p is 0, 1 or 2.

$C_1$-$C_6$alkyl and $C_1$-$C_4$alkyl groups include, for example, methyl (Me, $CH_3$), ethyl (Et, $C_2H_5$), n-propyl (n-Pr), isopropyl (i-Pr), n-butyl (n-Bu), isobutyl (i-Bu), sec-butyl and tert-butyl (t-Bu).

$C_3$-$C_6$cycloalkyl- includes cyclopropyl (c-propyl (c-Pr)), cyclobutyl (c-butyl (c-Bu)), cyclopentyl (c-pentyl) and cyclohexyl (c-hexyl).

$C_1$-$C_3$alkoxy- includes, for example, methoxy- and ethoxy-.

Halogen (or halo) encompasses fluorine, chlorine, bromine or iodine. The same correspondingly applies to halogen in the context of other definitions, such as haloalkyl.

$C_1$-$C_6$haloalkyl includes, for example, fluoromethyl-, difluoromethyl-, trifluoromethyl-, chloromethyl-, dichloromethyl-, trichloromethyl-, 2,2,2-trifluoroethyl-, 2,2-difluoroethyl, 1,1-difluoroethyl, 1,1,2,2-tetrafluoroethyl, 2-fluoroethyl-, 2-chloroethyl-, pentafluoroethyl-, 1,1-difluoro-2,2,2-trichloroethyl-, 2,2,3,3-tetrafluoroethyl-, 2,2,2-trichloroethyl-, heptafluoro-n-propyl and perfluoro-n-hexyl. $C_1$-$C_4$haloalkyl includes, for example, fluoromethyl-, difluoromethyl-, trifluoromethyl-, chloromethyl-, dichloromethyl-, trichloromethyl-, 2,2,2-trifluoroethyl-, 2-fluoroethyl-, 2-chloroethyl-, pentafluoroethyl-, 1,1-difluoro-2,2,2-trichloroethyl-2,2,3,3-tetrafluoroethyl-, 2,2,2-trichloroethyl- and heptafluoro-n-propyl-.

$C_1$-$C_4$alkoxy-$C_1$-$C_4$alkyl- includes, for example, methoxyethyl-.

$C_1$-$C_4$haloalkoxy-$C_1$-$C_4$alkyl- includes, for example, trifluoromethoxyethyl-.

$C_1$-$C_6$alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-$S(O)_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

In a preferred embodiment of the present invention, $R^1$ is selected from the group consisting of methyl, ethyl and n-propyl, preferably methyl.

In a preferred embodiment of the present invention, $R^2$ is selected from the group consisting of methyl, Cl, —$CF_3$ and —$SO_2$methyl, more preferably Cl.

In another preferred embodiment of the present invention, $R^3$ is —$CF_3$ or —$CHF_2$.

In one embodiment of the present invention, $R^4$ is selected from the group consisting of $C_1$-$C_6$alkyl- (e.g methyl, ethyl, n-propyl or i-propyl), $C_1$-$C_6$haloalkyl- (e.g $CHF_2CH_2$—), $C_1$-$C_3$alkoxy-$C_1$-$C_3$alkyl- (e.g methoxyethyl- or methoxypropyl-), $C_1$-$C_3$alkyl-$S(O)_pC_1$-$C_3$alkyl- (e.g $CH_3S(O)_2CH_2CH_2$—), cyano-$C_1$-$C_6$alkyl- (e.g —$CH_2CH_2CN$) and —$(CH_2)_n$—$CHR^6R^7$. In a preferred embodiment $R^4$ is $C_1$-$C_6$ alkyl, preferably methyl or ethyl and most preferably ethyl.

In another embodiment of the present invention $R^5$ is hydrogen or $C_1$-$C_4$alkyl- (preferably methyl), preferably hydrogen.

In another embodiment of the present invention, $R^4$ and $R^5$ together are —$(CH_2)_m$— wherein m is 2 or 3 (e.g —$CH_2CH_2$— or —$CH_2CH_2CH_2$—).

In another embodiment of the present invention $R^4$ is —$(CH_2)_n$—$CHR^6R^7$ wherein $R^6$ and $R^7$ together are selected from the group consisting of —$CH_2$—X—$CH_2$—, —$CH_2$—X—$CH_2$—$CH_2$—, —$CH_2CH_2$—X—$CH_2CH_2$—, wherein X is O, $S(O)_p$ or $NR^8$ and $R^8$ is hydrogen, $C_1$-$C_6$alkoxy- or —C(O)$C_1$-$C_6$alkyl. In one embodiment, $R^6$ and $R^7$ together form $-CH_2-O-CH_2-$. In another embodiment $R^6$ and $R^7$ together form $-CH_2-O-CH_2-CH_2-$. In another embodiment $R^6$ and $R^7$ together form $-CH_2CH_2-O-CH_2CH_2-$. In another embodiment, $R^6$ and $R^7$ together form $-CH_2-N(R^8)-CH_2-$. In another embodiment $R^6$ and $R^7$ together form $-CH_2-N(R)-CH_2-CH_2-$. In another embodiment $R^6$ and $R^7$ together form $-CH_2CH_2-N(R)-CH_2CH_2-$. R is hydrogen, $C_1$-$C_6$alkoxy- or $-C(O)C_1$-$C_6$alkyl, preferably $-C(O)$methyl. n is 0, 1 2 or 3, preferably 0.

Compounds of Formula (I) (and certain intermediate compounds used to synthesise compound of Formula (I)) may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

The present invention also includes all possible geometric and tautomeric forms of a compound of formula (I).

The present invention also includes agronomically acceptable salts that the compounds of Formula (I) may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound of the present invention and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The compounds of present invention can also be used in mixture with one or more additional herbicides and/or plant growth regulators. Examples of such additional herbicides or plant growth regulators include acetochlor, acifluorfen (including acifluorfen-sodium), aclonifen, ametryn, amicarbazone, aminopyralid, aminotriazole, atrazine, beflubutamid-M, benquitrione, bensulfuron (including bensulfuron-methyl), bentazone, bicyclopyrone, bilanafos, bipyrazone, bispyribac-sodium, bixlozone, bromacil, bromoxynil, butachlor, butafenacil, carfentrazone (including carfentrazone-ethyl), cloransulam (including cloransulam-methyl), chlorimuron (including chlorimuron-ethyl), chlorotoluron, chlorsulfuron, cinmethylin, clacyfos, clethodim, clodinafop (including clodinafop-propargyl), clomazone, clopyralid, cyclopyranil, cyclopyrimorate, cyclosulfamuron, cyhalofop (including cyhalofop-butyl), 2,4-D (including the choline salt and 2-ethylhexyl ester thereof), 2,4-DB, desmedipham, dicamba (including the aluminium, aminopropyl, bis-aminopropylmethyl, choline, dichloroprop, diglycolamine, dimethylamine, dimethylammonium, potassium and sodium salts thereof) diclosulam, diflufenican, diflufenzopyr, dimethachlor, dimethenamid-P, dioxopyritrione, diquat dibromide, diuron, epyrifenacil, ethalfluralin, ethofumesate, fenoxaprop (including fenoxaprop-P-ethyl), fenoxasulfone, fenpyrazone, fenquinotrione, fentrazamide, flazasulfuron, florasulam, florpyrauxifen (including florpyrauxifen-benzyl), fluazifop (including fluazifop-P-butyl), flucarbazone (including flucarbazone-sodium), flufenacet, flumetsulam, flumioxazin, fluometuron, flupyrsulfuron (including flupyrsulfuron-methyl-sodium), fluroxypyr (including fluroxypyr-meptyl), fomesafen, foramsulfuron, glufosinate (including L-glufosinate and the ammonium salts of both), glyphosate (including the diammonium, isopropylammonium and potassium salts thereof), halauxifen (including halauxifen-methyl), haloxyfop (including haloxyfop-methyl), hexazinone, hydantocidin, imazamox (including R-imazamox), imazapic, imazapyr, imazethapyr, indaziflam, iodosulfuron (including iodosulfuron-methyl-sodium), iofensulfuron (including iofensulfuron-sodium), ioxynil, isoproturon, isoxaflutole, lancotrione, MCPA, MCPB, mecoprop-P, mesosulfuron (including mesosulfuron-methyl), mesotrione, metamitron, metazachlor, methiozolin, metolachlor, metosulam, metribuzin, metsulfuron, napropamide, nicosulfuron, norflurazon, oxadiazon, oxasulfuron, oxyfluorfen, paraquat dichloride, pendimethalin, penoxsulam, phenmedipham, picloram, pinoxaden, pretilachlor, primisulfuron-methyl, prometryne, propanil, propaquizafop, propyrisulfuron, propyzamide, prosulfocarb, prosulfuron, pyraclonil, pyraflufen (including pyraflufen-ethyl), pyrasulfotole, pyridate, pyriftalid, pyrimisulfan, pyroxasulfone, pyroxsulam, quinclorac, quinmerac, quizalofop (including quizalofop-P-ethyl and quizalofop-P-tefuryl), rimisoxafen, rimsulfuron, saflufenacil, sethoxydim, simazine, S-metalochlor, sulfentrazone, sulfosulfuron, tebuthiuron, tefuryltrione, tembotrione, terbuthylazine, terbutryn, tetflupyrolimet, thiencarbazone, thifensulfuron, tiafenacil, tolpyralate, topramezone, tralkoxydim, triafamone, triallate, triasulfuron, tribenuron (including tribenuron-methyl), triclopyr, trifloxysulfuron (including trifloxysulfuron-sodium), trifludimoxazin, trifluralin, triflusulfuron, tripyrasulfone, 3-(2-chloro-4-fluoro-5-(3-methyl-2,6-dioxo-4-trifluoromethyl-3,6-dihydropyrimidin-1(2H)-yl)phenyl)-5-methyl-4,5-dihydroisoxazole-5-carboxylic acid ethyl ester, 4-hydroxy-1-methoxy-5-methyl-3-[4-(trifluoromethyl)-2-pyridyl]imidazolidin-2-one, 4-hydroxy-1,5-dimethyl-3-[4-(trifluoromethyl)-2-pyridyl]imidazolidin-2-one, 5-ethoxy-4-hydroxy-1-methyl-3-[4-(trifluoromethyl)-2-pyridyl]imidazolidin-2-one, 4-hydroxy-1-methyl-3-[4-(trifluoromethyl)-2-pyridyl]imidazolidin-2-one, 4-hydroxy-1,5-dimethyl-3-[1-methyl-5-(trifluoromethyl)pyrazol-3-yl]imidazolidin-2-one, (4R)1-(5-tert-butylisoxazol-3-yl)-4-ethoxy-5-hydroxy-3-methyl-imidazolidin-2-one, 4-amino-3-chloro-5-fluoro-6-(7-fluoro-1H-indol-6-yl)pyridine-2-carboxylic acid (including agrochemically acceptable esters thereof, for example, methyl 4-amino-3-chloro-5-fluoro-6-(7-fluoro-1H-indol-6-yl)pyridine-2-carboxylate, prop-2-ynyl 4-amino-3-chloro-5-fluoro-6-(7-fluoro-1H-indol-6-yl)pyridine-2-carboxylate and cyanomethyl 4-amino-3-chloro-5-fluoro-6-(7-fluoro-1H-indol-6-yl)pyridine-2-carboxylate), 3-ethylsulfanyl-N-(1,3,4-oxadiazol-2-yl)-5-(trifluoromethyl)-[1,2,4]triazolo[4,3-a]pyridine-8-carboxamide, 3-(isopropylsulfanylmethyl)-N-(5-methyl-1,3,4-oxadiazol-2-yl)-5-(trifluoromethyl)-[1,2,4]triazolo[4,3-a]pyridine-8-carboxamide, 3-(isopropylsulfonylmethyl)-N-(5-methyl-1,3,4-oxadiazol-2-yl)-5-(trifluoromethyl)-[1,2,4]triazolo[4,3-a]pyridine-8-carboxamide, 3-(ethylsulfonylmethyl)-N-(5-methyl-1,3,4-oxadiazol-2-yl)-5-(trifluoromethyl)-[1,2,4]triazolo[4,3-a]pyridine-8-carboxamide, ethyl 2-[[3-[[3-chloro-5-fluoro-6-[3-methyl-2,6-dioxo-4-(trifluoromethyl)pyrimidin-1-yl]-2-pyridyl]oxy]acetate and 6-chloro-4-(2,7-dimethyl-1-naphthyl)-5-hydroxy-2-methyl-pyridazin-3-one.

The mixing partners of the compound of Formula I may also be in the form of esters or salts, as mentioned e.g. in The Pesticide Manual, Sixteenth Edition, British Crop Protection Council, 2012.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds or mixtures of the present invention can also be used in combination with one or more herbicide safeners. Examples of such safeners include benoxacor, cloquintocet (including cloquintocet-mexyl), cyprosulfamide, dichlormid, fenchlorazole (including fenchlorazole-ethyl), fenclorim, fluxofenim, furilazole, isoxadifen (including isoxadifen-ethyl), mefenpyr (including mefenpyr-diethyl), metcamifen and oxabetrinil. Particularly preferred are mixtures of a compound of Formula I with cyprosulfamide, isoxadifen-ethyl, cloquintocet-mexyl and/or metcamifen.

The safeners of the compound of Formula I may also be in the form of esters or salts, as mentioned e.g. in The Pesticide Manual, $16^{th}$ Edition (BCPC), 2012. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of controlling weeds at a locus said method comprising application to the locus of a weed controlling amount of a composition comprising a compound of Formula (I). Moreover, the present invention further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally, the plants to be controlled are unwanted plants (weeds). 'Locus' means the area in which the plants are growing or will grow. Some crop plants may be inherently tolerant to herbicidal effects of compounds of Formula (I). However, in some instances tolerance may need to be engineered into the crop plant, for example by way of genetic engineering. Thus, it is possible that the crop plant is rendered tolerant to HPPD-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Cenchrus, Lolium, Festuca, Setaria, Ele-* usine, *Sorghum* or *Avena* species. Several HPPD-tolerant soybean transgenic "events" are known and include for example SYHT04R (WO2012/082542), SYHT0H$_2$ (WO2012/082548) and FG72. Other polynucleotide sequences that can be used to provide plants which are tolerant to the compounds of the present invention are disclosed in, for example, WO2010/085705 and WO2011/068567. Crop plants in which the composition according to the invention can be used thus include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Crop plants are to be understood as also including those crop plants which have been rendered tolerant to herbicides or classes of herbicides (e.g. ALS-, GS-, EPSPS-, PPO—, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crop plants are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crop plants are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica*, Viola and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

The compounds of the present invention can be prepared according to the following schemes.

Scheme 1

Compounds of Formula (I) may be prepared from anilines of Formula (II) and chloroformates of Formula (III).

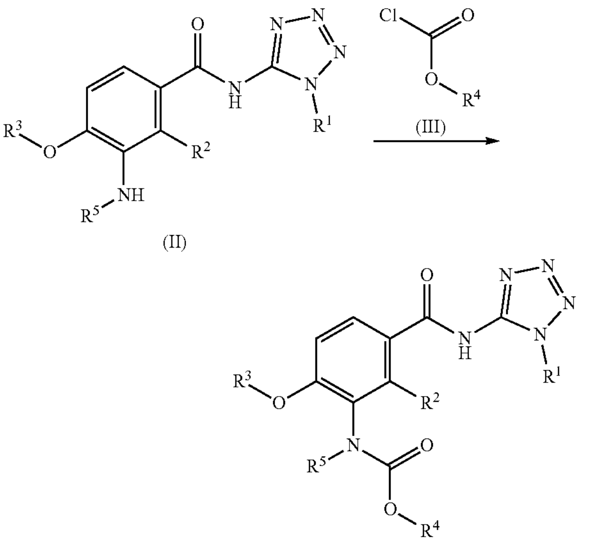

(II) (III) (I)

The compound of Formula (II) is treated with the compound of Formula (III) in a suitable solvent, for example acetonitrile, to give the compound of Formula (I).

Scheme 2

Compounds of Formula (II) may be prepared from compounds of Formula (IV) and amines of Formula (V).

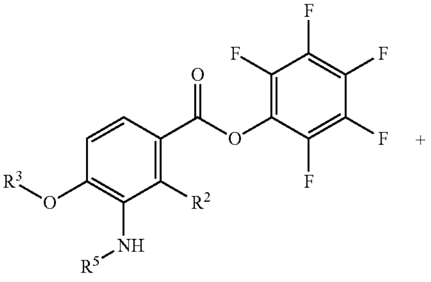

(IV)

-continued

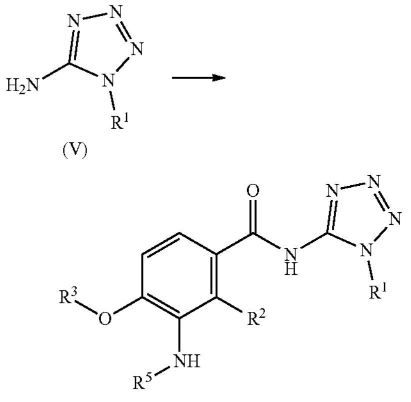

(V)

(II)

The compound of Formula (IV) and compound of Formula (V) are treated with a base, for example 2-tert-butylimino-2-diethylamino-1,3-dimethylperhydro-1,3,2-diazaphosphorine, in a suitable solvent, for example acetonitrile, to give the compound of Formula (II).

Scheme 3

Compounds of Formula (IV) may be prepared from benzoic acids of Formula (VI) and pentafluorophenol.

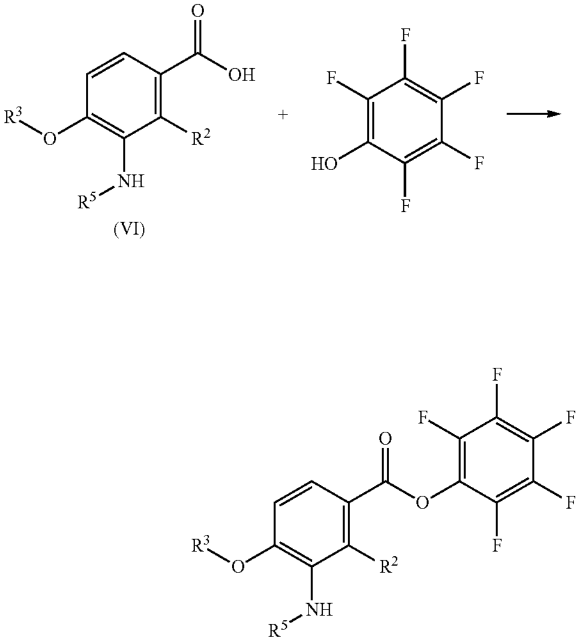

(VI)

(IV)

The compound of Formula (VI) is treated with pentafluorophenol and an ester coupling reagent, for example 1-ethyl-3-(3-dimethylaminopropyl)carbodiimide, in a suitable solvent, for example acetonitrile, to give the compound of Formula (IV).

Scheme 4

Compounds of Formula (VI) may be prepared from compounds of Formula (VII), where "Alk" is a $C_1$-$C_6$ alkyl group.

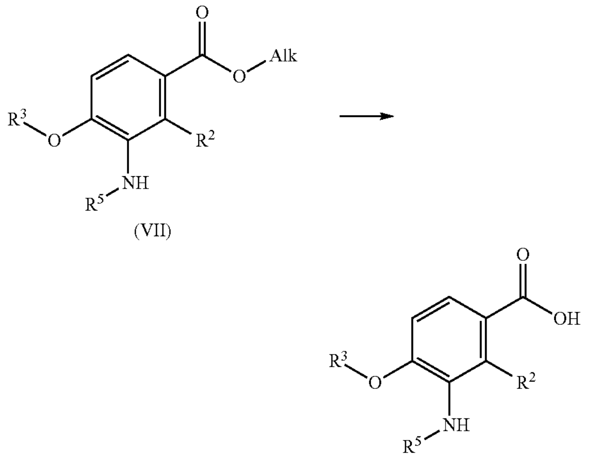

(VII)

(VI)

The compound of Formula (VII) is treated with a hydroxide base, for example lithium hydroxide, in a suitable solvent, for example a 4:1 mixture of tetrahydrofuran:water, to give the compound of Formula (VI).

Scheme 5

Compounds of Formula (VII) may be prepared from compounds of formula (VIII).

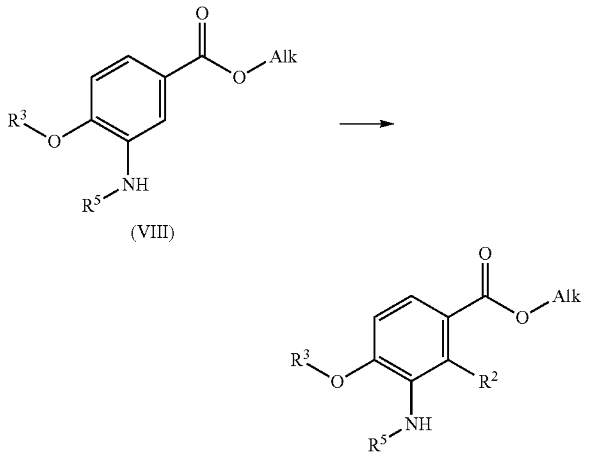

(VIII)

(VII)

The conditions used in this transformation will depend on the nature of $R^2$. For example, where $R^2$ is chlorine, the compound of Formula (VIII) is treated with sulfuryl chloride and a catalytic amount of diisopropylamine.

Alternatively, certain compounds of Formula (VII) may be prepared from compounds of Formula (VII), where $R^2$=chlorine. For example, a compound of Formula (VII) where $R^2$=chlorine may be treated with [1,3-bis(2,6-diisopropylphenyl)imidazol-2-ylidene](3-chloropyridyl)palladium(II) dichloride, trimethyl boroxine and potassium carbonate, in a suitable solvent, for example 1,4-dioxane, to give the corresponding compound of Formula (VII) where $R^2$=methyl.

Alternatively, compounds of Formula (I) may be prepared from compounds of Formula (IX) and alcohols of Formula (X).

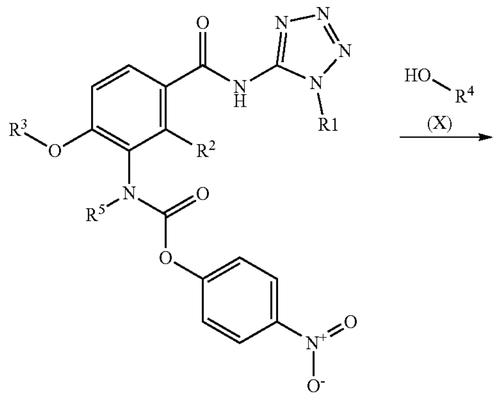

(IX)

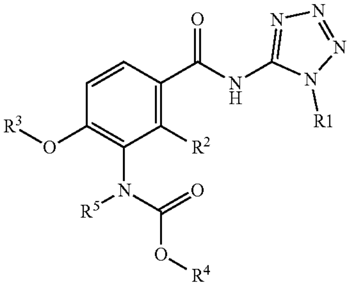

(I)

The compound of Formula (IX) is treated with the alcohol of Formula (X) in a suitable solvent, for example acetonitrile, to give the compound of Formula (I).

Compounds of formula (IX) may be prepared from anilines of formula (II) and p-nitrophenyl chloroformate:

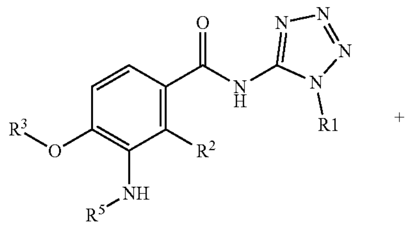

(II)

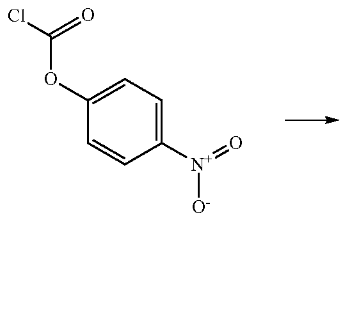

-continued

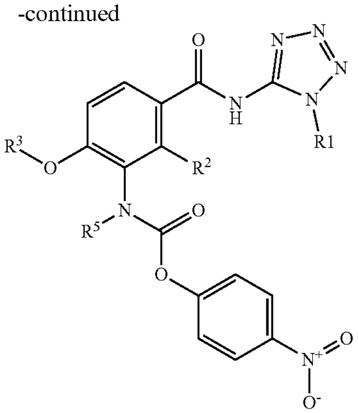

(IX)

The compound of Formula (II) is treated p-nitrophenyl chloroformate in a suitable solvent, for example acetonitrile, to give the compound of Formula (IX).

The following non-limiting examples provide specific synthesis methods for representative compounds of the present invention, as referred to the Table 1 provided herein.

PREPARATION OF COMPOUND 1.002

Step 1: Preparation of methyl 3-amino-2-chloro-4-(trifluoromethoxy)benzoate

To a round bottom flask containing methyl 3-amino-4-(trifluoromethoxy)benzoate (3.00 g, 12.8 mmol) was added toluene (45 mL) and diisopropylamine (0.13 g, 1.3 mmol). The reaction mixture was heated to 70° C. Sulfuryl chloride (1.55 g, 11.5 mmol) was added to the reaction mixture slowly over 10 min, and the reaction mixture quickly turned yellow and gas was released. After the addition was complete, the reaction mixture was stirred for an additional 40 min, then allowed to cool. Water (30 mL) was added and toluene was removed under reduced pressure. The reaction mixture was added to a separating funnel and extracted with ethyl acetate (2×60 mL). The combined organic layers were washed with brine (30 mL), dried over $MgSO_4$ and concentrated. The residue was purified via reverse phase column chromatography (acetonitrile+0.10% formic acid/water+0.1% formic acid gradient 40:60 to 80:20) to afford methyl 3-amino-2-chloro-4-(trifluoromethoxy)benzoate (1.88 g, 6.97 mmol, 55%) as a yellow oil. $^1H$ NMR (400 MHz, $CD_3OD$): δ=7.19 (dq, 1H), 7.07 (d, 1H), 3.89 (s, 3H).

Step 2: Preparation of 3-amino-2-chloro-4-(trifluoromethoxy)benzoic acid

To a stirred solution of methyl 3-amino-2-chloro-4-(trifluoromethoxy)benzoate (10.0 g, 37.1 mmol) in tetrahydrofuran (120 mL) and water (30.0 mL) at room temperature was added lithium hydroxide monohydrate (4.67 g, 111 mmol). The mixture was stirred at room temperature for 22 hours. The mixture was then cooled to 0° C. (ice-water bath). The reaction was quenched by slow addition of 2 M aq. HCl (100 mL). The cooling bath was removed and the mixture was allowed to warm to room temperature. EtOAc (100 mL) and brine (50 mL) were added and the phases were separated. The aqueous phase was extracted with EtOAc (100 mL). The combined organic phases were dried ($MgSO_4$), filtered and concentrated in vacuo to afford 3-amino-2-chloro-4-(trifluoromethoxy)benzoic acid (9.25 g, 34.4 mmol, 93%) as a beige solid which was used in the next step without further purification. $^1$H NMR (400 MHz, $CD_3OD$): δ=7.20-7.15 (m, 1H), 7.13-7.08 (m, 1H).

Step 3: Preparation of (2,3,4,5,6-pentafluorophenyl) 3-amino-2-chloro-4-(trifluoromethoxy)benzoate To a stirred suspension of 3-amino-2-chloro-4-(trifluoromethoxy)benzoic acid (9.24 g, 36.2 mmol) and 2,3,4,5,6-pentafluorophenol (7.32 g, 39.8 mmol) in dichloromethane (139 mL) at room temperature was added 3-(ethyliminomethyleneamino)-N,N-dimethyl-propan-1-amine hydrochloride (8.32 g, 43.4 mmol). The mixture was stirred at room temperature for one hour. The reaction was then quenched by addition of sat. aq. $NaHCO_3$ (100 mL). The mixture was stirred at room temperature for a further 5 minutes. Dichloromethane (40 mL) was added and the phases were separated. The aqueous phase was extracted with dichloromethane (50 mL). The combined organic phases were passed through a phase separator cartridge. The filtrate was adsorbed onto silica and the crude product was purified by flash column chromatography (cyclohexane/EtOAc gradient 98:2 to 93:7). Product-containing fractions were combined and concentrated in vacuo to afford (2,3,4,5,6-pentafluorophenyl) 3-amino-2-chloro-4-(trifluoromethoxy)benzoate (12.54 g, 29.74 mmol, 82%) as a pale yellow crystalline solid. $^1$H NMR (400 MHz, $CDCl_3$) δ=7.53 (d, 1H), 7.26-7.22 (m, 1H), 4.62 (br s, 2H).

Step 4: Preparation of 3-amino-2-chloro-N-(1-methyltetrazol-5-yl)-4-(trifluoromethoxy)benzamide To a stirred solution of (2,3,4,5,6-pentafluorophenyl) 3-amino-2-chloro-4-(trifluoromethoxy)benzoate (5.74 g, 13.6 mmol) in acetonitrile (115 mL) at room temperature was added 1-methyltetrazol-5-amine (2.97 g, 30.0 mmol) followed by 2-tert-butylimino-N,N-diethyl-1,3-dimethyl-1,3,2λ$^5$-diazaphosphinan-2-amine (8.47 g, 8.94 mL, 30.0 mmol). The mixture was stirred at room temperature for 30 minutes. The reaction was then quenched by addition of 2 M aq. HCl (100 mL). The mixture was stirred at room temperature for a further 30 minutes, then diluted with EtOAc (100 mL). The phases were separated. The aqueous phase was extracted with EtOAc (100 mL). The combined organic phases were washed with brine (100 mL), dried ($MgSO_4$), filtered and adsorbed onto C18-silica. The crude product was purified by reversed phase flash chromatography (acetonitrile+0.1% formic acid/water+0.1% formic acid gradient 35:65 to 55:45). Product-containing fractions were combined and partially concentrated in vacuo to remove acetonitrile. EtOAc (150 mL) was added and the phases were separated. The aqueous phase was extracted with EtOAc (150 mL). The combined organic phases were dried ($MgSO_4$), filtered and concentrated in vacuo to afford 3-amino-2-chloro-N-(1-methyltetrazol-5-yl)-4-(trifluoromethoxy)benzamide (4.24 g, 12.6 mmol, 93%) as an off-white solid. $^1$H NMR (400 MHz, $CD_3OD$): δ=7.27 (dq, 1H), 6.95 (d, 1H), 4.06 (s, 3H).

Step 5: Preparation of ethyl N-[2-chloro-3-[(1-methyltetrazol-5-yl)carbamoyl]-6-(trifluoromethoxy)phenyl]carbamate To a stirred solution of 3-amino-2-chloro-N-(1-methyltetrazol-5-yl)-4-(trifluoromethoxy)benzamide (250 mg, 0.743 mmol) in acetonitrile (2.50 mL) at room temperature was added ethyl chloroformate (1.41 mL, 14.9 mmol). The stirred mixture was heated to a gentle reflux (heating plate temperature 90° C.) for 69 hours. The mixture was allowed to cool to room temperature. Water (1 mL) was added. The mixture was stirred at room temperature for a further 15 minutes and was then diluted with EtOAc (20 mL), water (10 mL) and brine (10 mL). The phases were separated. The aqueous phase was extracted with EtOAc (20 mL). The combined organic phases were dried ($MgSO_4$), filtered and concentrated in vacuo. The crude product was partially purified by reversed phase flash chromatography (acetonitrile+0.10% formic acid/water+0.1% formic acid gradient 20:80 to 50:50). Product-containing fractions were combined, partially concentrated in vacuo to remove acetonitrile, then lyophilised to afford partially purified material. The partially purified material was then further purified by flash column chromatography (DCM/MeOH gradient 100:0 to 90:10). Clean fractions were combined and concentrated in vacuo to afford ethyl N-[2-chloro-3-[(1-methyltetrazol-5-yl)carbamoyl]-6-(trifluoromethoxy)phenyl]carbamate (104 mg, 0.242 mmol, 33%) as a white solid. $^1$H NMR (400 MHz, $CD_3OD$): δ=7.72 (d, 1H), 7.56-7.50 (m, 1H), 4.20 (q, 2H), 4.06 (s, 3H), 1.30 (t, 3H).

TABLE 1

Examples of herbicidal compounds of the present invention.

| Compound Number | Structure | 1H-NMR |
|---|---|---|
| 1.001 | 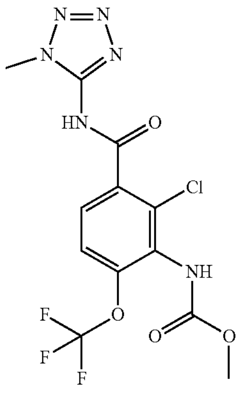 | 1H NMR (400 MHz, methanol-d4): 7.73 (d, 1H), 7.56-7.50 (m, 1H), 4.07 (s, 3H), 3.76 (s, 3H) |

TABLE 1-continued
Examples of herbicidal compounds of the present invention.
| Compound Number | Structure | 1H-NMR |
| --- | --- | --- |
| 1.002 | 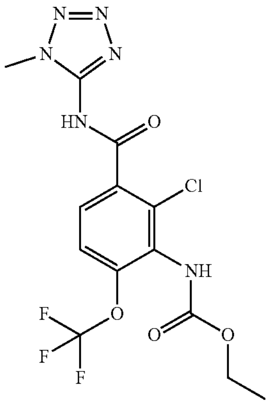 [SMILES: CCOC(=O)Nc1c(OC(F)(F)F)ccc(C(=O)Nc2nnnn2C)c1Cl] | 1H NMR (400 MHz, methanol-d4) 7.72 (d, 1H), 7.56-7.50 (m, 1H), 4.20 (q, 2H), 4.06 (s, 3H), 1.30 (t, 3H) |
| 1.003 | 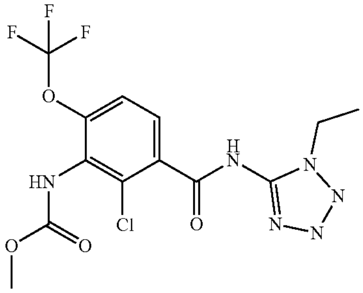 [SMILES: CCN1NNN=C1NC(=O)c1ccc(OC(F)(F)F)c(NC(=O)OC)c1Cl] | 1H NMR (400 MHz, methanol-d4): 7.72 (d, 1H), 7.55-7.50 (m, 1H), 4.42 (q, 2H), 3.76 (s, 3H), 1.58 (t, 3H) |
| 1.004 | 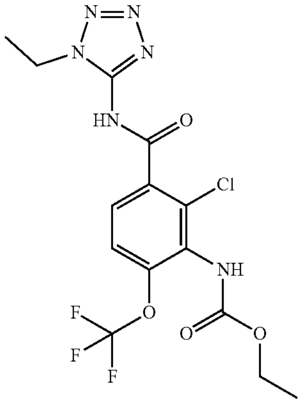 [SMILES: CCOC(=O)Nc1c(OC(F)(F)F)ccc(C(=O)Nc2nnnn2CC)c1Cl] | 1H NMR (400 MHz, methanol-d4): 7.72 (d, 1H), 7.56-7.50 (m, 1H), 4.43 (q, 2H), 4.20 (q, 2H), 1.58 (t, 3H), 1.30 (t, 3H) |
| 1.005 | 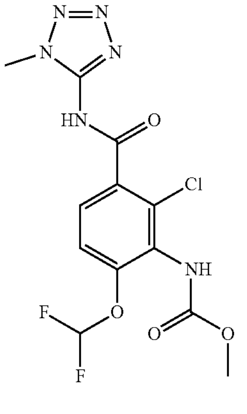 | 1H NMR (400 MHz, DMSO-d6): 11.87 (s, 1H), 9.29 (br s, 1H), 7.76 (d, 1H), 7.12-7.48 (m, 2H), 4.00 (s, 3H), 3.65 (s, 3H) |

TABLE 1-continued
| Compound Number | Structure | 1H-NMR |
|---|---|---|
| Examples of herbicidal compounds of the present invention. | | |
| 1.006 | 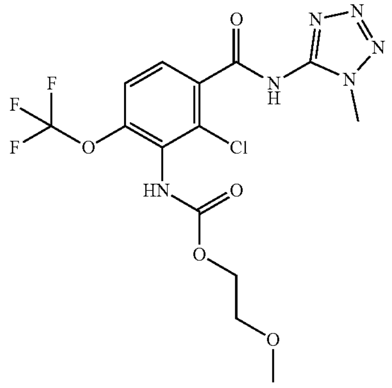 [SMILES: COCCOC(=O)Nc1c(OC(F)(F)F)ccc(C(=O)Nc2nnnn2C)c1Cl] | 1H NMR (400 MHz, methanol-d4): 7.73 (d, 1H), 7.56-7.50 (m, 1H), 4.32-4.25 (m, 2H), 4.06 (s, 3H), 3.69-3.58 (m, 2H), 3.38 (s, 3H) |
| 1.007 | 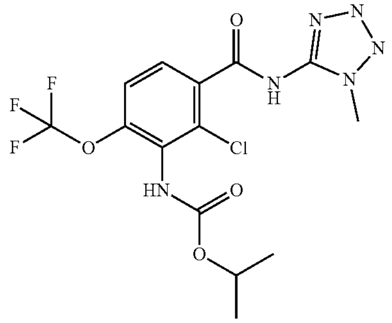 [SMILES: CC(C)OC(=O)Nc1c(OC(F)(F)F)ccc(C(=O)NC2=NNNN2C)c1Cl] | 1H NMR (400 MHz, methanol-d4): 7.72 (d, 1H), 7.52 (qd, 1H), 5.00-4.91 (m, 1H), 4.07 (s, 3H), 1.29 (br d, 6H) |
| 1.008 | 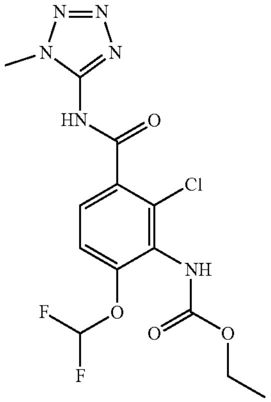 [SMILES: CCOC(=O)Nc1c(OC(F)F)ccc(C(=O)Nc2nnnn2C)c1Cl] | 1H NMR (400 MHz, DMSO-d6): 11.86 (s, 1H), 9.23 (br s, 1H), 7.74-7.76 (d, 1H), 7.11-7.47 (m, 2H), 4.10 (q, 2H), 4.00 (s, 3H), 1.17-1.26 (m, 3H) |
| 1.009 | 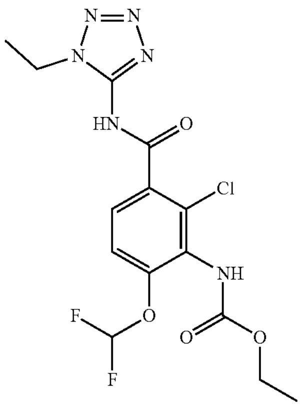 [SMILES: CCOC(=O)Nc1c(OC(F)F)ccc(C(=O)Nc2nnnn2CC)c1Cl] | 1H NMR (400 MHz, DMSO-d6): δ ppm 1.22 (t, 3H) 4.00 (s, 3H) 4.10 (q, 2H) 7.29 (t, 1H) 7.39 (d, 1H) 7.75 (d, 1H) 9.23 (br s, 1H) 11.86 (s, 1H) |

TABLE 1-continued
| Examples of herbicidal compounds of the present invention. | | |
|---|---|---|
| Compound Number | Structure | 1H-NMR |
| 1.010 | 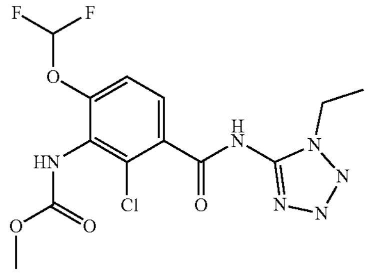 [SMILES: CCN1NNN=C1NC(=O)c1ccc(OC(F)F)c(NC(=O)OC)c1Cl] | 1H NMR (400 MHz, DMSO-d6): 11.98 (br s, 1H), 9.29 (br s, 1H), 7.74 (d, 1H), 7.40 (d, 1H), 7.30 (t, 1H), 4.35 (q, 2H), 3.64 (s, 3H), 1.47 (t, 3H) |
| 1.011 | 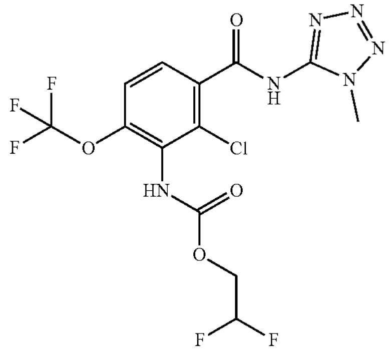 [SMILES: Cn1nnnc1NC(=O)c1ccc(OC(F)(F)F)c(NC(=O)OCC(F)F)c1Cl] | 1H NMR (400 MHz, acetonitrile-d3): 7.84-7.59 (m, 2H), 7.55-7.47 (m, 1H), 6.08 (tt, 1H), 4.38 (dt, 2H), 3.98 (s, 3H) |
| 1.012 | 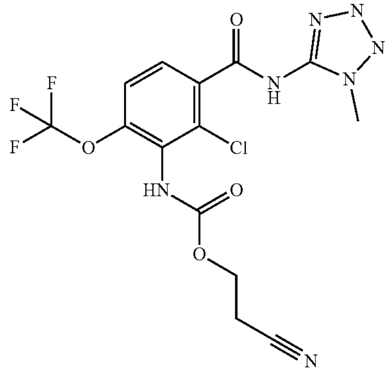 [SMILES: CN1NNN=C1NC(=O)c1ccc(OC(F)(F)F)c(NC(=O)OCCC#N)c1Cl] | 1H NMR (400 MHz, methanol-d4): 7.75 (d, 1H), 7.57-7.51 (m, 1H), 4.35 (t, 2H), 4.06 (s, 3H), 2.87 (br t, 2H) |
| 1.013 | 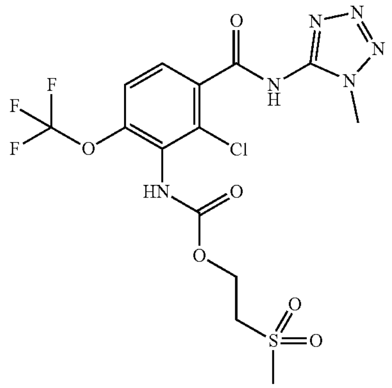 [SMILES: Cn1nnnc1NC(=O)c1ccc(OC(F)(F)F)c(NC(=O)OCCS(C)(=O)=O)c1Cl] | 1H NMR (400 MHz, methanol-d4): 7.75 (d, 1H), 7.58-7.52 (m, 1H), 4.58 (t, 2H), 4.07 (s, 3H), 3.51 (br t, 2H), 3.03 (br s, 3H) |

TABLE 1-continued
| Examples of herbicidal compounds of the present invention. | | |
|---|---|---|
| Compound Number | Structure | 1H-NMR |
| 1.014 | 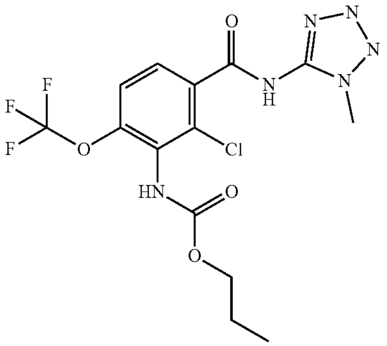 [SMILES: CCCOC(=O)Nc1c(OC(F)(F)F)ccc(C(=O)NC2=NNNN2C)c1Cl] | 1H NMR (400 MHz, methanol-d4): 7.73 (d, 1H), 7.56-7.50 (m, 1H), 4.12 (t, 2H), 4.07 (s, 3H), 1.70 (sxt, 2H), 0.98 (t, 3H) |
| 1.015 | 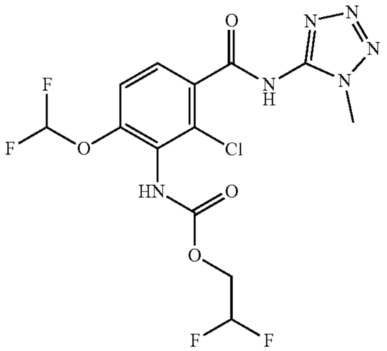 [SMILES: Cn1nnnc1NC(=O)c1ccc(OC(F)F)c(NC(=O)OCC(F)F)c1Cl] | 1H NMR (400 MHz, acetonitrile-d3): 7.67 (d, 1H), 7.57 (br s, 1H), 7.34 (d, 1H), 6.82 (t, 1H), 6.08 (tt, 1H), 4.37 (dt, 2H), 3.97 (s, 3H) |
| 1.016 | 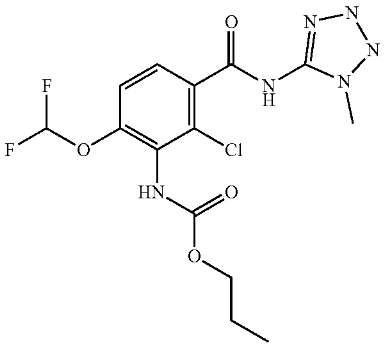 [SMILES: CCCOC(=O)Nc1c(OC(F)F)ccc(C(=O)NC2=NNNN2C)c1Cl] | 1H NMR (400 MHz, methanol-d4): 7.67 (d, 1H), 7.37 (d, 1H), 6.90 (t, 1H), 4.11 (t, 2H), 4.06 (s, 3H), 1.70 (sxt, 2H), 0.99 (t, 3H) |
| 1.017 | 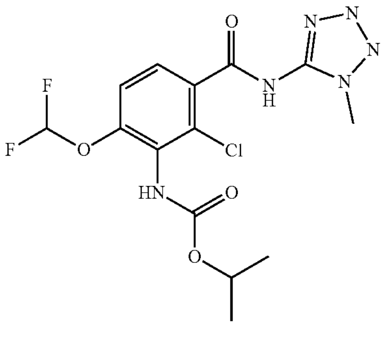 [SMILES: CC(C)OC(=O)Nc1c(OC(F)F)ccc(C(=O)NC2=NNNN2C)c1Cl] | 1H NMR (400 MHz, acetonitrile-d3): 7.64 (d, 1H), 7.32 (d, 1H), 7.17 (br s, 1H), 6.80 (t, 1H), 4.90 (spt, 1H), 3.97 (s, 3H), 1.26 (d, 6H) |

TABLE 1-continued
| Compound Number | Structure | 1H-NMR |
|---|---|---|
| Examples of herbicidal compounds of the present invention. | | |
| 1.018 | 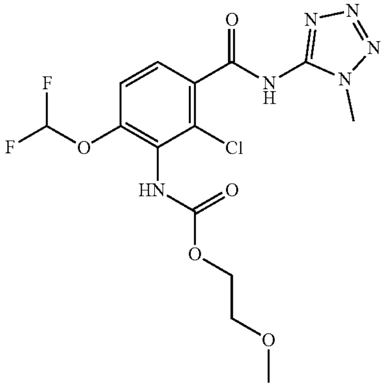 [SMILES: COCCOC(=O)Nc1c(OC(F)F)ccc(C(=O)Nc2nnnn2C)c1Cl] | 1H NMR (400 MHz, methanol-d4): 7.67 (d, 1H), 7.37 (d, 1H), 6.90 (t, 1H), 4.31-4.24 (m, 2H), 4.06 (s, 3H), 3.68-3.59 (m, 2H), 3.38 (s, 3H) |
| 1.019 | 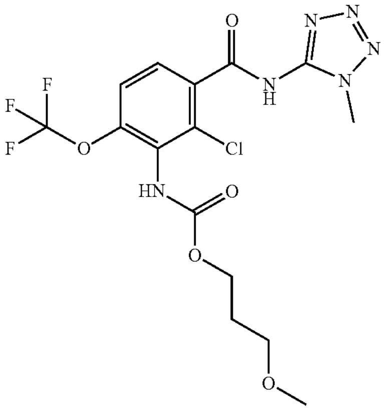 [SMILES: COCCCOC(=O)Nc1c(OC(F)(F)F)ccc(C(=O)Nc2nnnn2C)c1Cl] | 1H NMR (400 MHz, methanol-d4): 7.73 (d, 1H), 7.57-7.50 (m, 1H), 4.23 (t, 2H), 4.07 (s, 3H), 3.49 (br t, 2H), 3.34 (s, 3H), 1.92 (quin, 2H) |
| 1.020 | 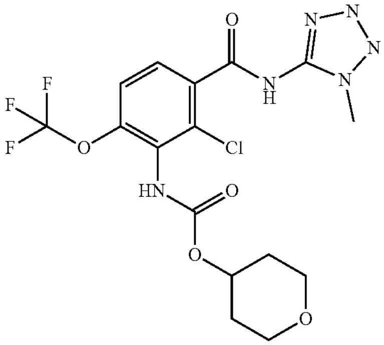 [SMILES: CN1NNN=C1NC(=O)c1ccc(OC(F)(F)F)c(NC(=O)OC2CCOCC2)c1Cl] | 1H NMR (400 MHz, chloroform-d): 10.55 (br s, 1H), 7.77 (d, 1H), 7.45-7.39 (m, 1H), 6.44 (s, 1H), 4.95 (tt, 1H), 4.12 (s, 3H), 3.97-3.88 (m, 2H), 3.55 (ddd, 2H), 2.04-1.94 (m, 2H), 1.81-1.67 (m, 2H + overlaps with water peak) |
| 1.021 | 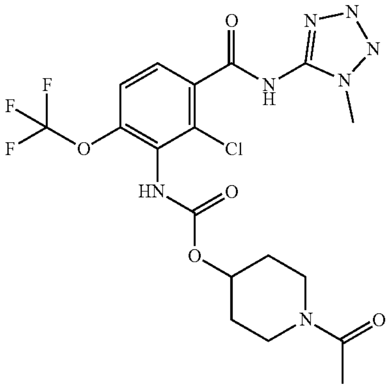 [SMILES: CC(=O)N1CCC(OC(=O)Nc2c(OC(F)(F)F)ccc(C(=O)NC3=NNNN3C)c2Cl)CC1] | 1H NMR (400 MHz, methanol-d4): 7.74 (d, 1H), 7.57-7.51 (m, 1H), 4.97 (tt, 1H), 4.07 (s, 3H), 3.88-3.61 (m, 2H), 3.59-3.43 (m, 2H), 2.12 (s, 3H), 2.07-1.86 (m, 2H), 1.84-1.59 (m, 2H) |

TABLE 1-continued
| Compound Number | Structure | 1H-NMR |
|---|---|---|
| 1.022 | 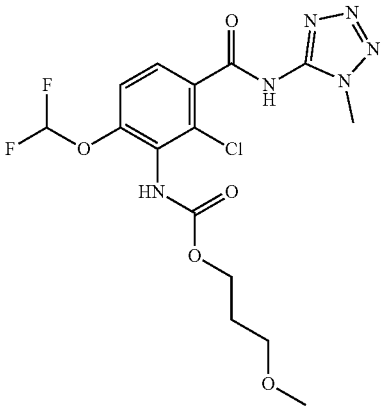 [SMILES: COCCCOC(=O)Nc1c(OC(F)F)ccc(C(=O)Nc2nnnn2C)c1Cl] | 1H NMR (400 MHz, methanol-d4): 7.67 (d, 1H), 7.37 (d, 1H), 6.91 (t, 1H), 4.22 (t, 2H), 4.06 (s, 3H), 3.50 (br t, 2H), 3.34 (s, 3H), 1.93 (quin, 2H) |
| 1.023 | 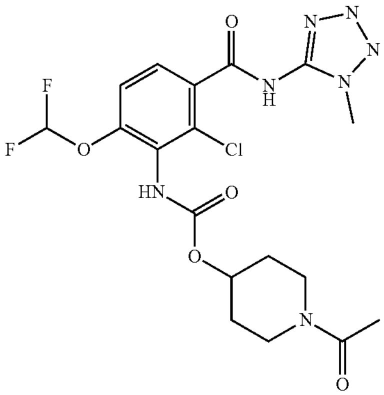 [SMILES: CC(=O)N1CCC(OC(=O)Nc2c(OC(F)F)ccc(C(=O)NC3=NNNN3C)c2Cl)CC1] | 1H NMR (400 MHz, methanol-d4): 7.69 (d, 1H), 7.38 (d, 1H), 6.92 (t, 1H), 4.96 (tt, 1H), 4.06 (s, 3H), 3.88-3.65 (m, 2H), 3.57-3.44 (m, 2H), 2.12 (s, 3H), 2.07-1.86 (m, 2H), 1.85-1.63 (m, 2H) |
| 1.024 | 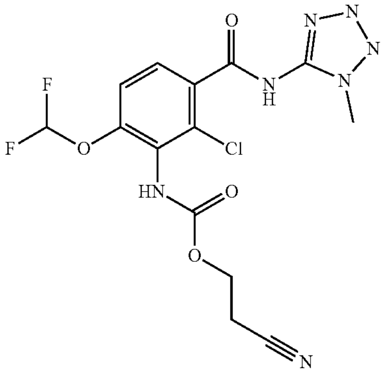 [SMILES: CN1NNN=C1NC(=O)c1ccc(OC(F)F)c(NC(=O)OCCC#N)c1Cl] | 1H NMR (400 MHz, methanol-d4): 7.69 (d, 1H), 7.38 (d, 1H), 6.92 (t, 1H), 4.35 (t, 2H), 4.05 (s, 3H), 2.87 (br t, 2H) |
| 1.025 | 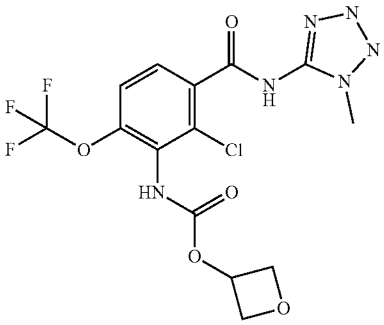 [SMILES: CN1NNN=C1NC(=O)c1ccc(OC(F)(F)F)c(NC(=O)OC2COC2)c1Cl] | |

TABLE 1-continued
Examples of herbicidal compounds of the present invention.
| Compound Number | Structure | 1H-NMR |
|---|---|---|
| 1.026 | 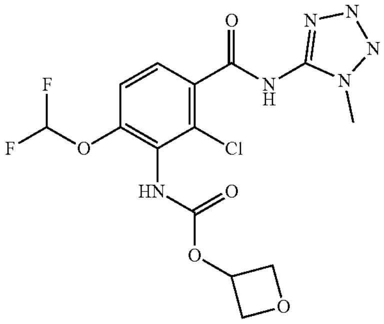 [SMILES: CN1NNN=C1NC(=O)c1ccc(OC(F)F)c(NC(=O)OC2COC2)c1Cl] | 1H NMR (400 MHz, acetonitrile-d3): δ = 7.66 (d, 1H), 7.52 (br s, 1H), 7.33 (d, 1H), 6.82 (t, 1H), 5.45-5.36 (m, 1H), 4.83 (t, 2H), 4.56 (dd, 2H), 3.97 (s, 3H). |
| 1.027 | 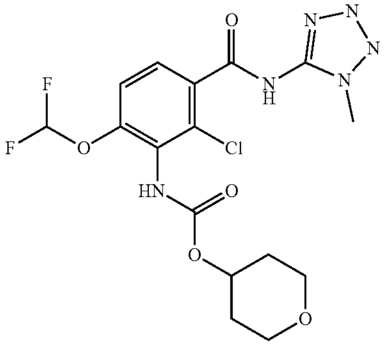 [SMILES: CN1NNN=C1NC(=O)c1ccc(OC(F)F)c(NC(=O)OC2CCOCC2)c1Cl] | 1H NMR (400 MHz, chloroform-d): δ = 10.90 (br s, 1H), 7.72 (d, 1H), 7.30 (d, 1H), 6.80-6.39 (m, 2H), 4.92 (tt, 1H), 4.10 (s, 3H), 3.99-3.87 (m, 2H), 3.55 (ddd, 2H), 2.05-1.94 (m, 2H), 1.89-1.52 (m, 2H + overlaps with H2O peak). |
| 1.028 | 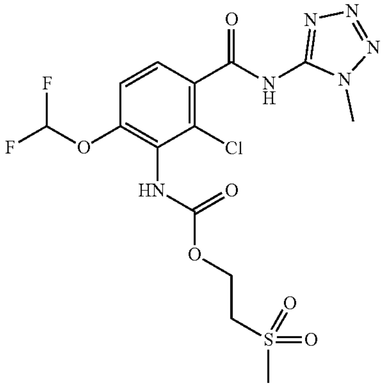 [SMILES: Cn1nnnc1NC(=O)c1ccc(OC(F)F)c(NC(=O)OCCS(C)(=O)=O)c1Cl] | 1H NMR (400 MHz, methanol-d4): δ = 7.69 (d, 1H), 7.38 (d, 1H), 6.94 (t, 1H), 4.57 (t, 2H), 4.05 (s, 3H), 3.50 (br t, 2H), 3.03 (br s, 3H). |
| 1.029 | 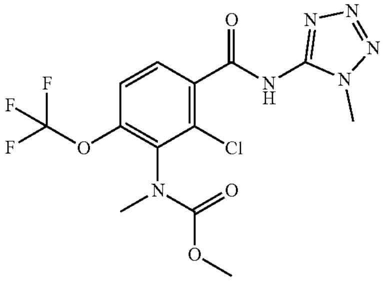 [SMILES: COC(=O)N(C)c1c(OC(F)(F)F)ccc(C(=O)Nc2nnnn2C)c1Cl] | 1H NMR (400 MHz, DMSO-d6) δ ppm 11.94 (br s, 1 H) 7.91 (d, 1 H) 7.71 (d, 1 H) 4.00 (s, 3 H) 3.56 (s, 3 H) 3.12 (s, 3 H) |

TABLE 1-continued
Examples of herbicidal compounds of the present invention.
| Compound Number | Structure | 1H-NMR |
|---|---|---|
| 1.030 | 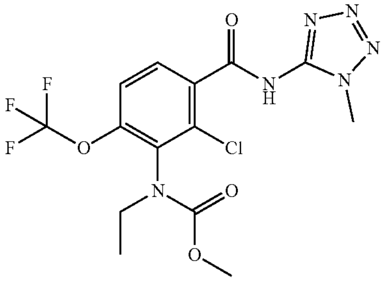 [SMILES: CCN(C(=O)OC)c1c(OC(F)(F)F)ccc(C(=O)Nc2nnnn2C)c1Cl] | 1H NMR (400 MHz, DMSO-d6) δ ppm 11.94 (br s, 1H) 7.90 (d, 1H) 7.69 (br d, 1H) 4.00 (s, 3H) 3.56 (s, 3H), 3.50-3.63 (m, 2H) 1.09 (t, 3H) |
| 1.031 | 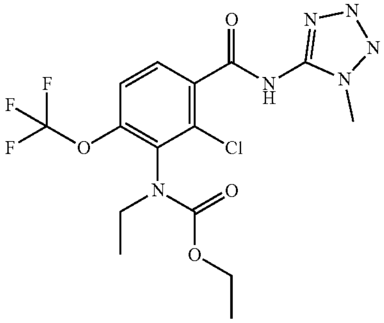 [SMILES: CCOC(=O)N(CC)c1c(OC(F)(F)F)ccc(C(=O)NC2=NNNN2C)c1Cl] | 1H NMR (400 MHz, DMSO-d6) δ ppm 11.95 (br s, 1H) 7.90 (d, 1H) 7.69 (br dd, 1H) 4.09 (m, 3H) 3.88-4.12 (m, 2H) 3.49-3.69 (m, 2H) 0.99-1.16 (m, 6H) |
| 1.032 | 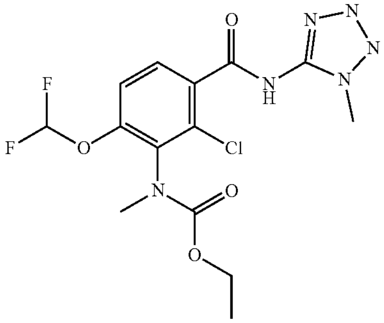 [SMILES: CCOC(=O)N(C)c1c(OC(F)F)ccc(C(=O)NC2=NNNN2C)c1Cl] | 1H NMR (400 MHz, DMSO-d6) δ ppm 11.96 (br s, 1H) 7.91 (d, 1H) 7.70 (br dd, 1H) 4.01 (s, 3H) 3.97-4.10 (m, 2H) 3.11 (s, 3H) 1.07 (t, 3H) |
| 1.033 | 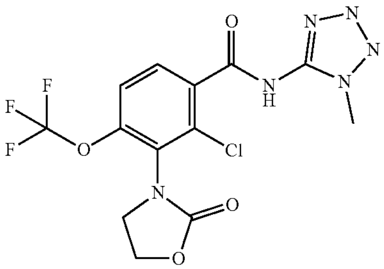 [SMILES: CN1NNN=C1NC(=O)c1ccc(OC(F)(F)F)c(N2CCOC2=O)c1Cl] | 1H NMR (400 MHz, DMSO-d6) δ ppm 11.98 (s, 1H), 7.99 (d, 1H), 7.75 (d, 1H), 4.53-4.70 (m, 2H) 4.02 (br s, 4H), 3.85 (m, 1H). |
| 1.034 | 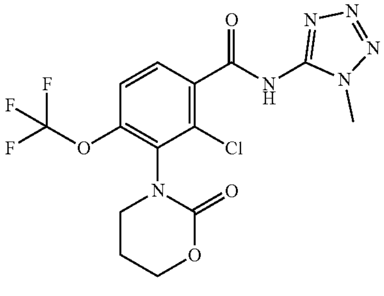 [SMILES: Cn1nnnc1NC(=O)c1ccc(OC(F)(F)F)c(N2CCCOC2=O)c1Cl] | 1H NMR (400 MHz, DMSO-d6) δ ppm 11.96 (br s, 1H), 7.92 (d, 1H), 7.70 (d, 1H), 4.43 (m, 2H), 4.00 (s, 3H), 3.51 (m, 2H), 2.15 (m, 2H). |

TABLE 1-continued
| Examples of herbicidal compounds of the present invention. | | |
|---|---|---|
| Compound Number | Structure | 1H-NMR |
| 1.035 | 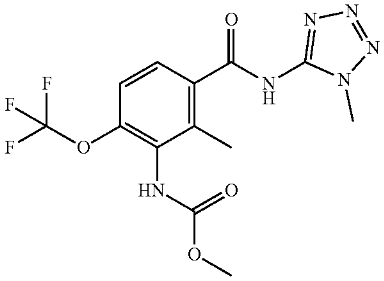 [SMILES: COC(=O)Nc1c(OC(F)(F)F)ccc(C(=O)Nc2nnnn2C)c1C] | 1H NMR (400 MHz, methanol-d4): δ = 7.68 (d, 1H), 7.40-7.34 (m, 1H), 4.05 (s, 3H), 3.75 (br s, 3H), 2.41 (s, 3H). |
| 1.036 | 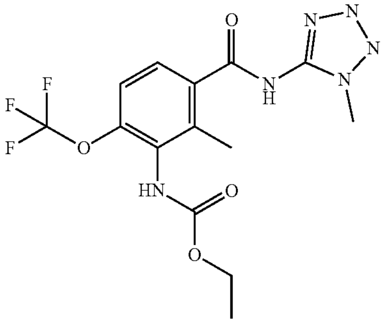 [SMILES: CCOC(=O)Nc1c(OC(F)(F)F)ccc(C(=O)NC2=NNNN2C)c1C] | 1H NMR (400 MHz, methanol-d4): δ = 7.68 (d, 1H), 7.40-7.33 (m, 1H), 4.24-4.13 (m, 2H), 4.05 (s, 3H), 2.42 (s, 3H), 1.30 (br s, 3H). |
| 1.037 | 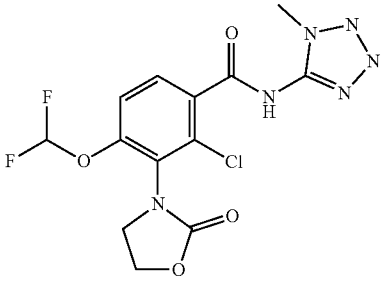 [SMILES: CN1NNN=C1NC(=O)c1ccc(OC(F)F)c(N2CCOC2=O)c1Cl] | 1H NMR (400 MHz, DMSO-d6) δ ppm 11.91 (s, 1H), 7.92 (d, 1H), 7.51 (d, 1H), 7.42 (t, 1H), 4.54-4.64 (m, 2H), 4.00 (s, 3H), 3.81-3.97 (m, 2H). |
| 1.038 | 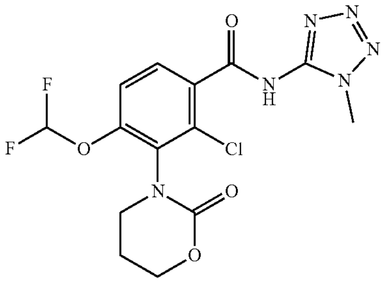 [SMILES: Cn1nnnc1NC(=O)c1ccc(OC(F)F)c(N2CCCOC2=O)c1Cl] | 1H NMR (400 MHz, DMSO-d6) δ ppm 11.85 (s, 1H), 7.86 (d, 1H), 7.49 (d, 1H), 7.39 (t, 1H), 4.40 (m, 2H), 3.99 (s, 3H), 3.47 (m, 2H), 2.15 (m, 2H). |
| 1.039 | 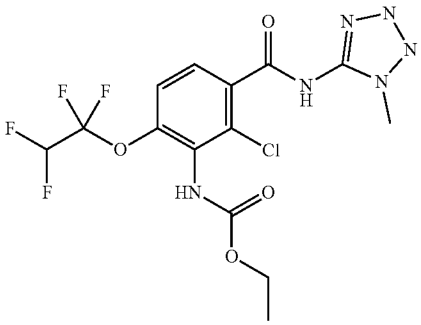 [SMILES: CCOC(=O)Nc1c(OC(F)(F)C(F)F)ccc(C(=O)NC2=NNNN2C)c1Cl] | 1H NMR (400 MHz, methanol) δ = 7.70 (d, 1H), 7.53 (d, 1H), 6.36 (tt, 1H), 4.23-4.14 (m, 2H), 4.07 (s, 3H), 1.34-1.24 (m, 3H). |

TABLE 1-continued
Examples of herbicidal compounds of the present invention.
| Compound Number | Structure | 1H-NMR |
| --- | --- | --- |
| 1.040 | 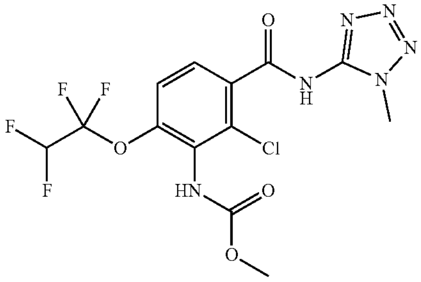 [SMILES: COC(=O)Nc1c(OC(F)(F)C(F)F)ccc(C(=O)Nc2nnnn2C)c1Cl] | 1H NMR (400 MHz, methanol-d4): δ = 7.71 (d, 1H), 7.53 (d, 1H), 6.37 (tt, 1H), 4.06 (s, 3H), 3.74 (s, 3H). |
| 1.041 | 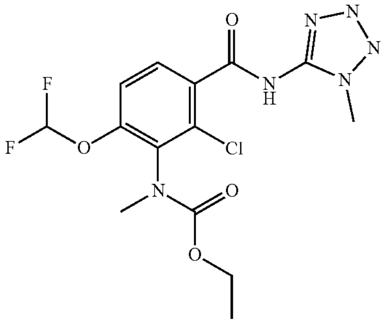 [SMILES: CCOC(=O)N(C)c1c(OC(F)F)ccc(C(=O)NC2=NNNN2C)c1Cl] | 1H NMR (400 MHz, DMSO-d6) δ ppm 11.88 (s, 1H), 7.84 (d, 1H), 7.47 (d, 1H), 7.43 (t, 1H), 4.01-4.06 (m, 2H), 3.99 (s, 3H), 3.08 (s, 3H), 1.07 (t, 3H). |
| 1.042 | 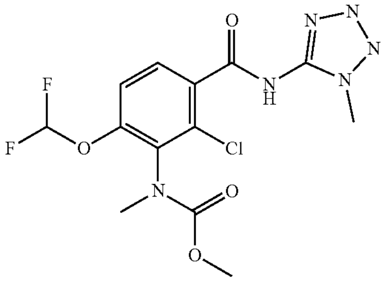 [SMILES: COC(=O)N(C)c1c(OC(F)F)ccc(C(=O)NC2=NNNN2C)c1Cl] | 1H NMR (400 MHz, DMSO-d6) δ ppm 11.88 (s, 1H), 7.86 (d, 1H), 7.50 (d, 1H), 7.43 (t, 1H), 4.01 (s, 3H), 3.35 (s, 3H), 3.09 (s, 3H) |
| 1.043 | 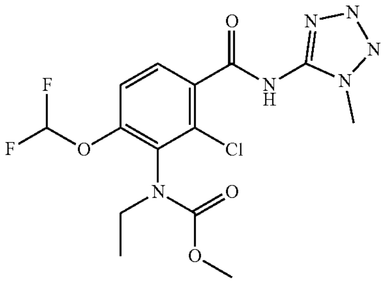 [SMILES: CCN(C(=O)OC)c1c(OC(F)F)ccc(C(=O)NC2=NNNN2C)c1Cl] | 1H NMR (400 MHz, DMSO-d6) δ ppm 11.87 (s, 1H), 7.84 (d, 1H), 7.47 (d, 1H), 7.44 (t, 1H), 4.00 (s, 3H), 3.62-3.67 (m, 1H), 3.55 (s, 3H), 3.45-3.54 (m, 1H), 1.08 (t, 3H). |
| 1.044 | 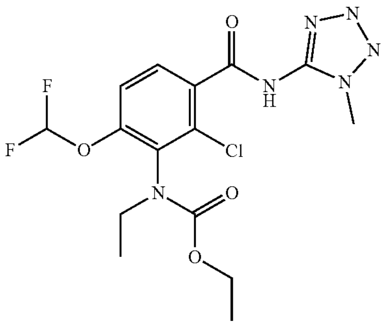 [SMILES: CCOC(=O)N(CC)c1c(OC(F)F)ccc(C(=O)NC2=NNNN2C)c1Cl] | 1H NMR (400 MHz, DMSO-d6) δ ppm 11.88 (s, 1H), 7.83 (d, 1H), 7.45 (d, 1H), 7.43 (t, 1H), 4.00-4.09 (m, 2H), 3.99 (s, 3H), 3.61-3.70 (m, 1H) 3.46-3.51 (m, 1H), 1.11 (t, 3H), 1.07 (t, 3H). |

Biological Examples

Seeds of a variety of test species are sown in standard soil in pots (*Lolium perenne* (LOLPE), *Amaranthus retoflexus* (AMARE), *Abutilon theophrasti* (ABUTH), *Setaria faberi* (SETFA), *Echinochloa crus-galli* (ECHCG), *Ipomoea hederacea* (IPOHE)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 125 g/h unless otherwise indicated. The test plants are then grown in a glasshouse under controlled conditions in a glasshouse (at 24/16° C., day/night; 14 hours light; 65% humidity) and watered twice daily. After 13 days for pre and post-emergence, the test is evaluated for the percentage damage caused to the plant. The biological activities are shown in the following table on a five-point scale (5=80-100%; 4=60-79%; 3=40-59%; 2=20-39%; 1=0-19%). "—" denotes not tested on this species or data not captured.

The invention claimed is:

1. A compound pf Formula (I):

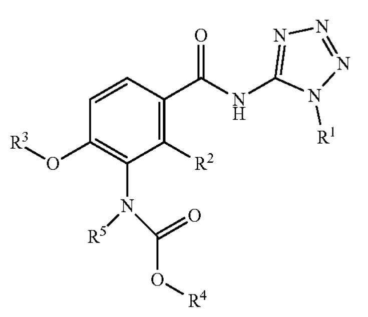

(I)

or an agronomically acceptable salt thereof, wherein:

$R^1$ is selected from the group consisting of $C_1$-$C_4$alkyl-, $C_1$-$C_4$haloalkyl-, $C_1$-$C_4$alkoxy-$C_1$-$C_4$alkyl- and $C_1$-$C_4$haloalkoxy-$C_1$-$C_4$alkyl-;

$R^2$ is selected from the group consisting of halogen, $C_1$-$C_6$alkyl-, $C_1$-$C_6$alkoxy-, $C_1$-$C_6$ haloalkyl- and —$S(O)_pC_1$-$C_6$alkyl;

$R^3$ is $C_1$-$C_6$haloalkyl;

TABLE B1

| | POST Application | | | | | PRE Application | | | | |
|---|---|---|---|---|---|---|---|---|---|---|
| Compound | AMARE | ABUTH | SETFA | ECHCG | IPOHE | AMARE | ABUTH | SETFA | ECHCG | IPOHE |
| 1.001 | 5 | 5 | 5 | 5 | 5 | 5 | 5 | 5 | 5 | 3 |
| 1.002 | 4 | 4 | 4 | 4 | 4 | 5 | 5 | 4 | 5 | 5 |
| 1.003 | 4 | 4 | 4 | 4 | 4 | 5 | 5 | 5 | 5 | 4 |
| 1.004 | 4 | 4 | 4 | 4 | 4 | 5 | 5 | 3 | 5 | 4 |
| 1.005 | 5 | 5 | 5 | 5 | 5 | 5 | 5 | 4 | 5 | 4 |
| 1.006 | 5 | 5 | 4 | 4 | 4 | 4 | 5 | 4 | 5 | 4 |
| 1.007 | 4 | 5 | 4 | 4 | 4 | 5 | 5 | 4 | 5 | 4 |
| 1.008 | 4 | 4 | 4 | 4 | 4 | 5 | 5 | 4 | 5 | 4 |
| 1.009 | 4 | 4 | 3 | 5 | 4 | 5 | 5 | 3 | 4 | 4 |
| 1.010 | 4 | 3 | 5 | 5 | 4 | 3 | 5 | 3 | 3 | 4 |
| 1.011 | 4 | — | 5 | 5 | 4 | 5 | — | 5 | 5 | 4 |
| 1.012 | 5 | — | 5 | 5 | 5 | 5 | — | 5 | 5 | 4 |
| 1.013 | 4 | — | 5 | 5 | 2 | 5 | — | 2 | 2 | 2 |
| 1.014 | 4 | — | 5 | 5 | 4 | 3 | — | 4 | 4 | 2 |
| 1.015 | 5 | — | 5 | 5 | 4 | 5 | — | 5 | 5 | 3 |
| 1.016 | 4 | — | 5 | 5 | 3 | 5 | — | 3 | 4 | 2 |
| 1.017 | 5 | — | 5 | 5 | 5 | 5 | — | 5 | 5 | 4 |
| 1.018 | 4 | — | 5 | 5 | 4 | 4 | — | 3 | 4 | 2 |
| 1.019 | 5 | — | 5 | 5 | 4 | 3 | — | 2 | 5 | 4 |
| 1.020 | 5 | — | 5 | 5 | 5 | 5 | — | 5 | 5 | 5 |
| 1.021 | 4 | — | 4 | 5 | 2 | 3 | — | 1 | 1 | 2 |
| 1.022 | 5 | — | 5 | 5 | 4 | 5 | — | 4 | 4 | 4 |
| 1.023 | 4 | — | 2 | 3 | 1 | 3 | — | 1 | 1 | 2 |
| 1.024 | 5 | — | 5 | 5 | 4 | 5 | — | 3 | 4 | 5 |
| 1.026 | 5 | — | — | 5 | 5 | 5 | — | 3 | 5 | 4 |
| 1.027 | 5 | — | 5 | 5 | 5 | 4 | — | 5 | 4 | 4 |
| 1.028 | 5 | — | — | 2 | 3 | 5 | — | 1 | 3 | 2 |
| 1.029 | 5 | — | — | 5 | 5 | 5 | — | 5 | 5 | 5 |
| 1.030 | 5 | — | — | 5 | 5 | 5 | — | 5 | 5 | 4 |
| 1.031 | 5 | — | 5 | 5 | 5 | 5 | — | 5 | 5 | 5 |
| 1.032 | 5 | — | 5 | 5 | 5 | 5 | — | 5 | 5 | 5 |
| 1.035 | 5 | — | 5 | 5 | 3 | 5 | — | 5 | 5 | 3 |
| 1.036 | 5 | — | 5 | 5 | 5 | 5 | — | 5 | 5 | 5 |
| 1.037 | 5 | — | 5 | 5 | 5 | 5 | — | 5 | 5 | 5 |
| 1.041 | 5 | — | 5 | 5 | 5 | 5 | — | 4 | 5 | 4 |
| 1.042 | 5 | — | 5 | 5 | 5 | 5 | — | 5 | 5 | 4 |
| 1.043 | 5 | — | 5 | 5 | 4 | 5 | — | 5 | 5 | 3 |
| 1.044 | 5 | — | 5 | 5 | 4 | 5 | — | 4 | 5 | 2 |

$R^4$ is selected from the group consisting of $C_1$-$C_6$alkyl-, $C_1$-$C_6$haloalkyl-, $C_1$-$C_3$alkoxy-$C_1$-$C_3$alkyl-, $C_1$-$C_4$haloalkoxy-$C_1$-$C_4$alkyl-, $C_1$-$C_4$alkoxy-$C_1$-$C_4$haloalkyl-, $C_1$-$C_3$alkyl-$S(O)_p$$C_1$-$C_3$alkyl-, cyano-$C_1$-$C_6$alkyl-, $-(CH_2)_n-CHR^6R^7$, $C_3$-$C_6$cycloalkyl- and $C_3$-$C_6$cycloalkyl-$C_1$-$C_3$alkyl- wherein either $C_3$-$C_6$cycloalkyl- may be optionally substituted by one or two fluorine atoms; and $R^5$ is selected from the group consisting of hydrogen, $C_1$-$C_6$alkyl-, $C_1$-$C_6$haloalkyl and $C_3$-$C_6$cycloalkyl; or $R^4$ and $R^5$ together are $-(CH_2)_m-$, and $R^6$ and $R^7$ together with the carbon atom to which they are attached form a saturated 4-, 5- or 6-membered heterocycle which is optionally substituted; and m is 2 or 3, n is 0, 1, 2 or 3, and p is 0, 1 or 2.

2. A compound according to claim 1, wherein $R^1$ is selected from the group consisting of methyl, ethyl and n-propyl.

3. A compound according to claim 1, wherein $R^2$ is selected from the group consisting of methyl, Cl, $-CF_3$ and $-SO_2$methyl.

4. A compound according to claim 3, wherein $R^2$ is Cl.

5. A compound according to claim 1, wherein $R^3$ is $-CF_3$ or $-CHF_2$.

6. A compound according to claim 1, wherein $R^4$ is selected from the group consisting of $C_1$-$C_6$alkyl-, $C_1$-$C_6$haloalkyl-, $C_1$-$C_6$alkoxy-$C_1$-$C_3$alkyl-, $C_1$-$C_3$alkyl-$S(O)_p$$C_1$-$C_3$alkyl-, cyano-$C_1$-$C_6$alkyl- and $-(CH_2)_n-CHR^6R^7$.

7. A compound according to claim 1, wherein $R^5$ is hydrogen or $C_1$-$C_4$alkyl-.

8. A compound according to claim 1, wherein $R^4$ and $R^5$ together are $-(CH_2)_m-$.

9. A compound according to claim 1, wherein $R^6$ and $R^7$ together are selected from the group consisting of $-CH_2-X-CH_2-$, $-CH_2-X-CH_2-CH_2-$, $-CH_2CH_2-X-CH_2CH_2-$, wherein X is O, S(O) p or $NR^8$ and $R^8$ is hydrogen, $C_1$-$C_6$alkoxy- or $-C(O)$ $C_1$-$C_6$alkyl.

10. A herbicidal composition comprising a compound according to claim 1 and an agriculturally acceptable formulation adjuvant.

11. A herbicidal composition according to claim 10, further comprising at least one additional pesticide.

12. A herbicidal composition according to claim 11, wherein the additional pesticide is a herbicide or herbicide safener.

13. A method of controlling weeds at a locus comprising application to the locus of a weed controlling amount of a composition according to claim 10.

14. A method of making a compound of Formula (I) of claim 1, comprising reacting a compound of Formula (II)

(II)

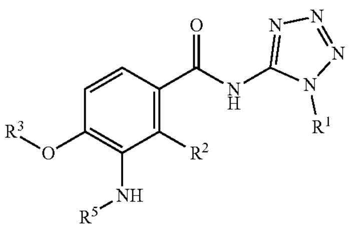

with a compound of Formula (III)

(III)

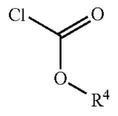

wherein:

$R^1$ is selected from the group consisting of $C_1$-$C_4$alkyl-, $C_1$-$C_4$haloalkyl-, $C_1$-$C_4$alkoxy-$C_1$-$C_4$alkyl- and $C_1$-$C_4$haloalkoxy-$C_1$-$C_4$alkyl-;

$R^2$ is selected from the group consisting of halogen, $C_1$-$C_6$alkyl-, $C_1$-$C_3$alkoxy-, $C_1$-$C_6$ haloalkyl- and $-S(O)$, $C_1$-$C_6$alkyl;

$R^3$ is $C_1$-$C_6$haloalkyl;

$R^4$ is selected from the group consisting of $C_1$-$C_6$alkyl-, $C_1$-$C_6$haloalkyl-, $C_1$-$C_3$alkoxy-$C_1$-$C_3$alkyl-, $C_1$-$C_4$haloalkoxy-$C_1$-$C_4$alkyl-, $C_1$-$C_4$alkoxy-$C_1$-$C_4$haloalkyl-, $C_1$-$C_3$alkyl-$S(O)_p$$C_1$-$C_3$alkyl-, cyano-$C_1$-$C_6$alkyl-, $-(CH_2)_n-CHR^6R^7$, $C_3$-$C_6$cycloalkyl- and $C_3$-$C_6$cycloalkyl-$C_1$-$C_3$alkyl- wherein either $C_3$-$C_6$cycloalkyl- may be optionally substituted by one or two fluorine atoms; and $R^5$ is selected from the group consisting of hydrogen, $C_1$-$C_6$alkyl-, $C_1$-$C_6$haloalkyl and $C_3$-$C_6$cycloalkyl;

$R^6$ and $R^7$ together with the carbon atom to which they are attached form a saturated 4-, 5- or 6-membered heterocycle which is optionally substituted;

n is 0, 1, 2 or 3, and p is 0, 1 or 2.

15. A compound of Formula (II):

(II)

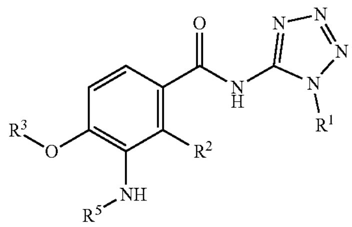

$R^1$ is selected from the group consisting of $C_1$-$C_4$alkyl-, $C_1$-$C_4$haloalkyl-, $C_1$-$C_4$alkoxy-$C_1$-$C_4$alkyl- and $C_1$-$C_4$haloalkoxy-$C_1$-$C_4$alkyl-;

$R^2$ is selected from the group consisting of halogen, $C_1$-$C_6$alkyl-, $C_1$-$C_3$alkoxy-, $C_1$-$C_6$ haloalkyl- and $-S(O)_p$$C_1$-$C_6$alkyl;

$R^3$ is $C_1$-$C_6$haloalkyl;

$R^5$ is selected from the group consisting of hydrogen, $C_1$-$C_6$alkyl-, $C_1$-$C_6$haloalkyl and $C_3$-$C_6$cycloalkyl; and p is 0, 1 or 2.

16. The compound of claim 15, wherein $R^1$ is methyl, ethyl, or n-propyl.

17. The compound of claim 15, wherein $R^2$ is methyl, Cl, $-CF_3$, or $-SO_2$methyl.

18. The compound of claim 15, wherein $R^3$ is $-CF_3$, or $-CHF_2$.

19. The compound of claim 15, wherein $R^5$ is hydrogen or $C_1$-$C_4$alkyl-.
20. A compound selected from the group consisting of:
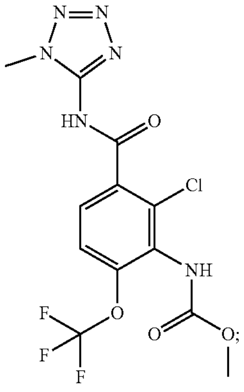
;
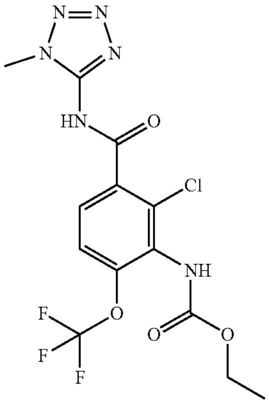
;
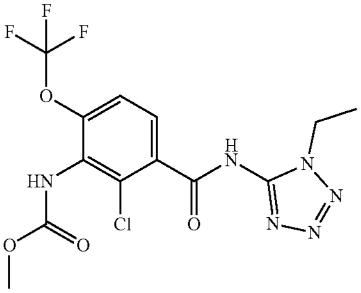
;
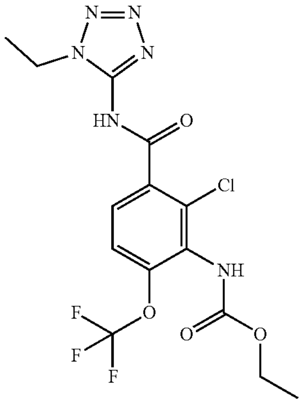
;
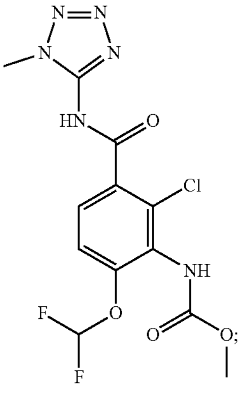
;
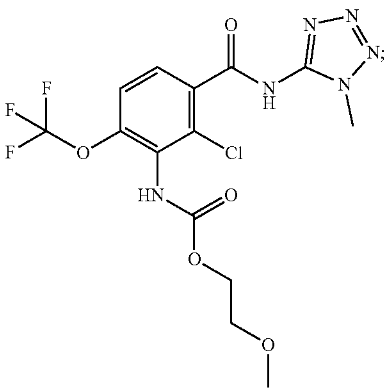
;
-continued
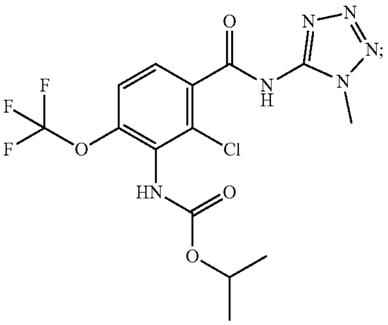
;
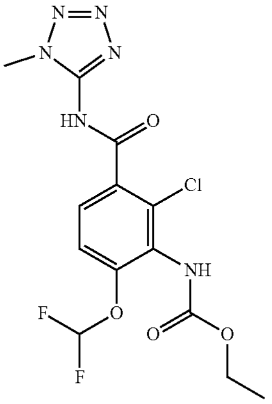
;
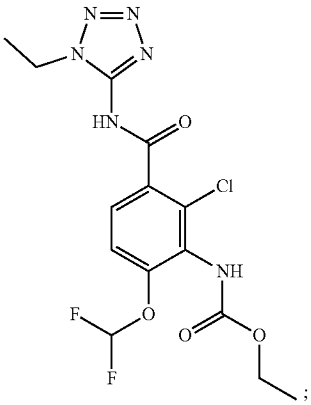
;
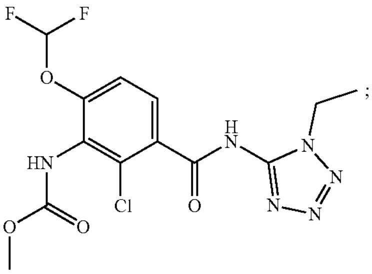
;

-continued
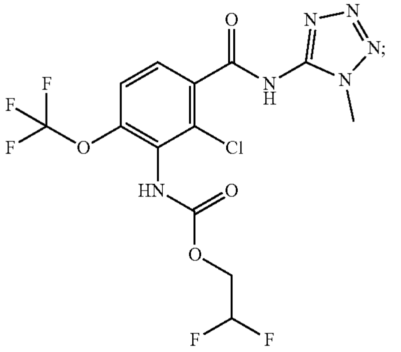
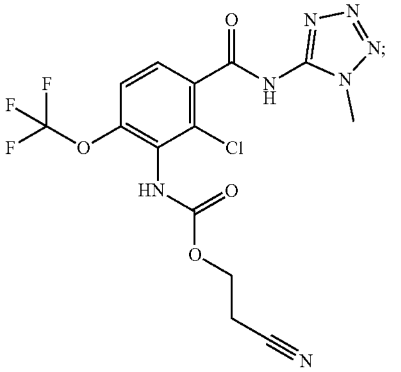
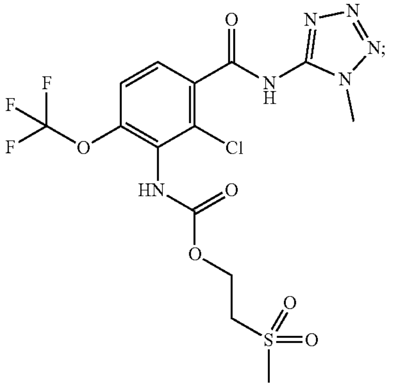
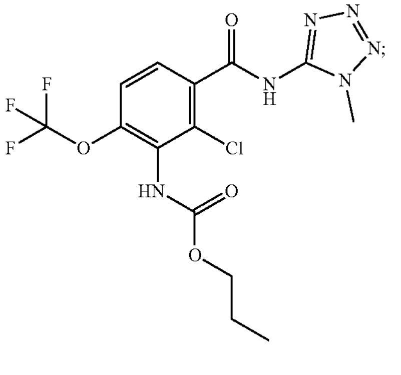
-continued
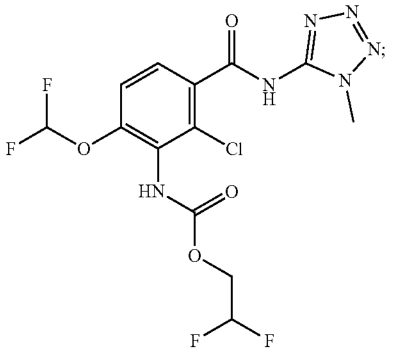
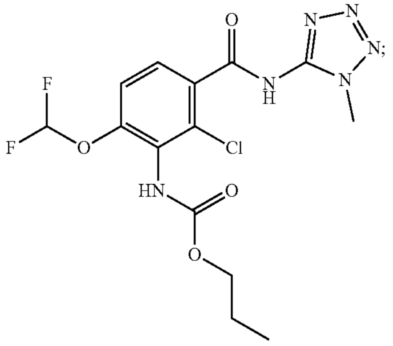
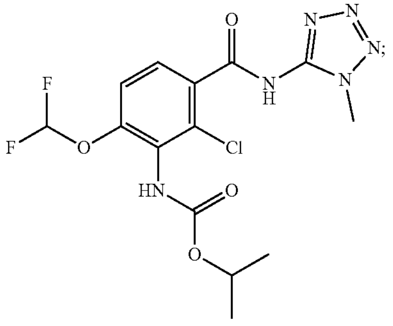
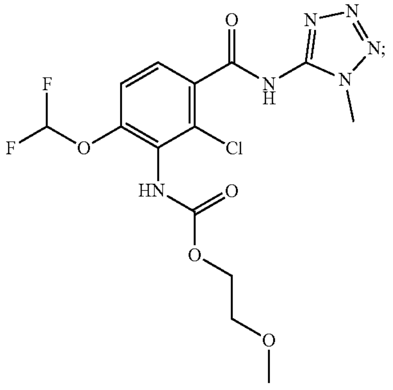

-continued
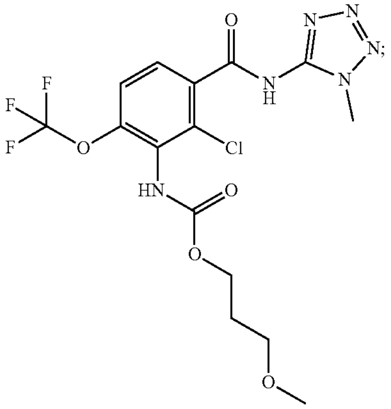
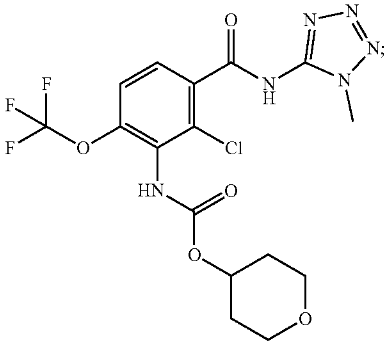
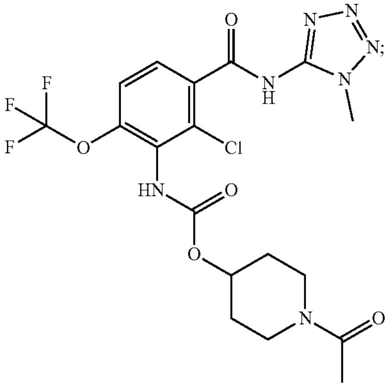
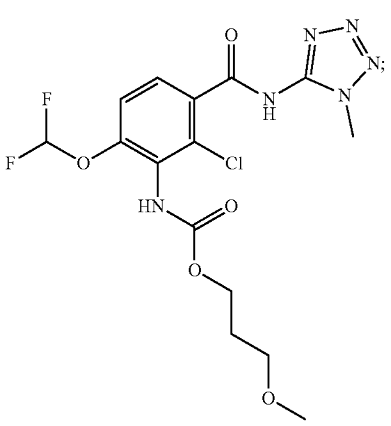
-continued
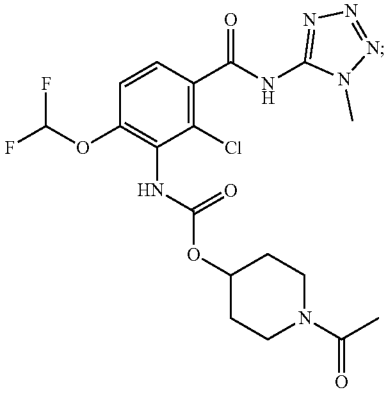 [SMILES: CC(=O)N1CCC(OC(=O)Nc2c(OC(F)F)ccc(C(=O)Nc3nnnn3C)c2Cl)CC1]
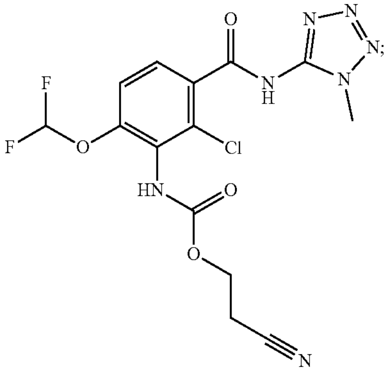
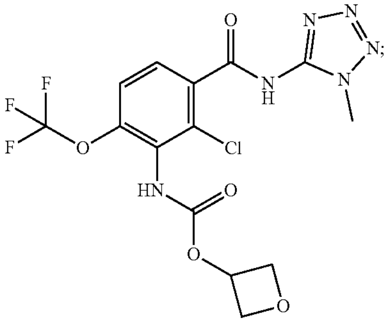
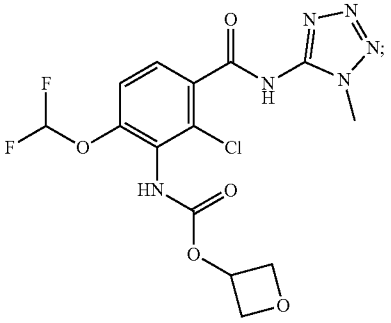

-continued
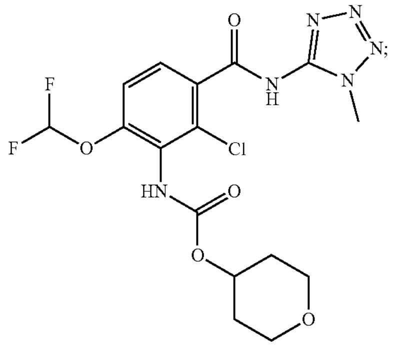
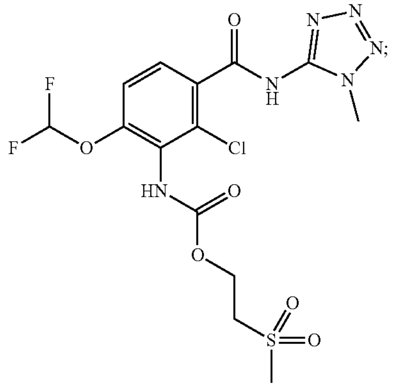
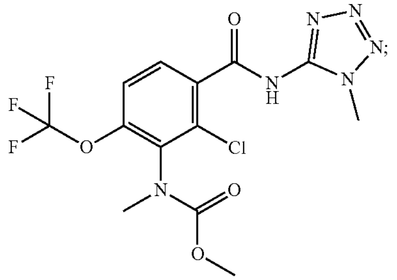
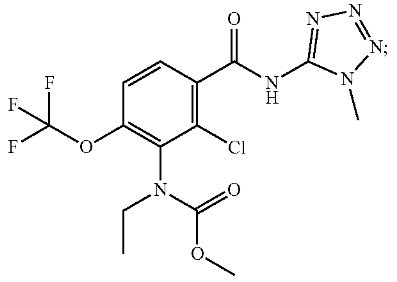
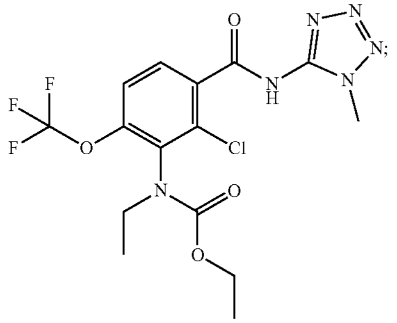
-continued
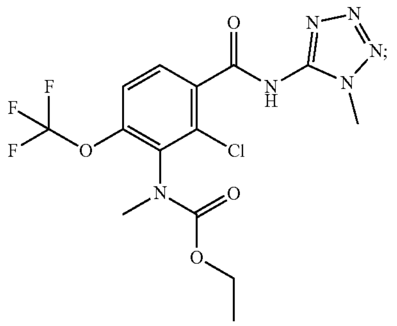
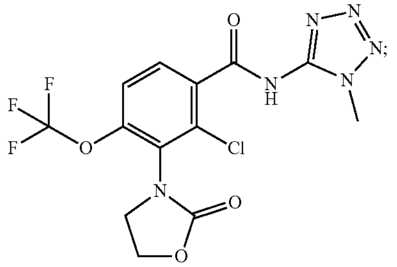
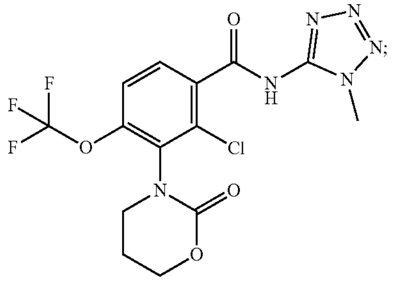
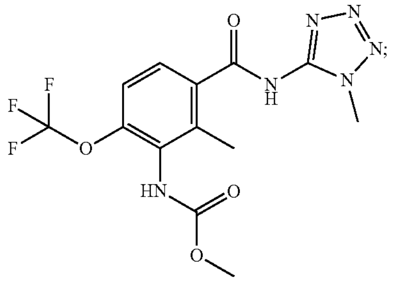
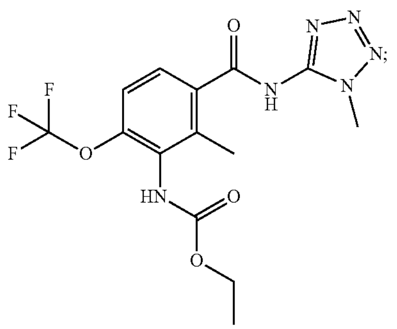

-continued
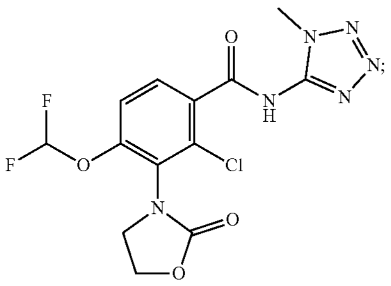
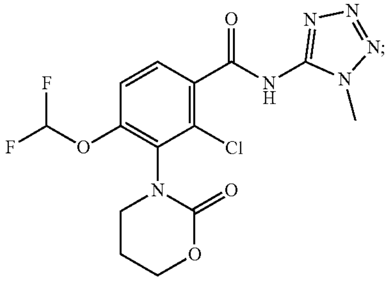
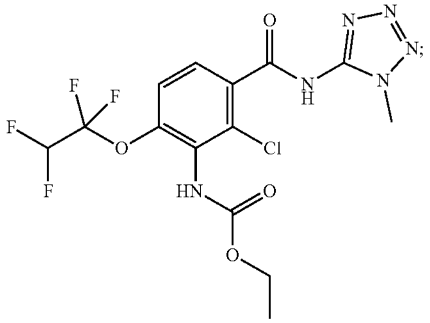
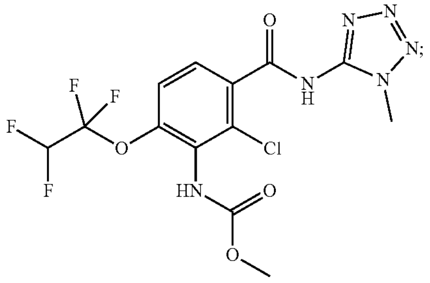
-continued
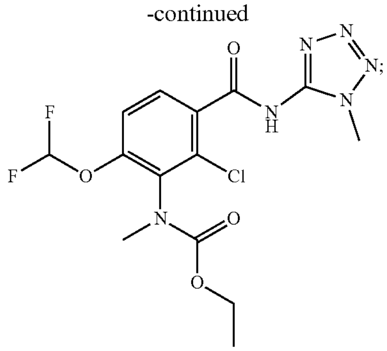
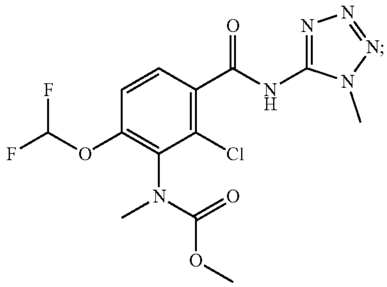
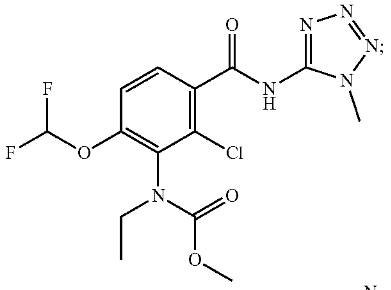
and
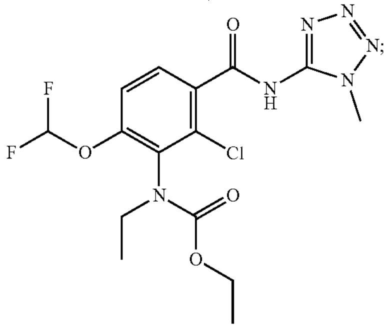
or an agronomically acceptable salt thereof.
* * * * *